(12) United States Patent
Doyle et al.

(10) Patent No.: US 6,297,238 B1
(45) Date of Patent: Oct. 2, 2001

(54) THERAPEUTIC AGENTS

(75) Inventors: Kevin Doyle, Nottingham (GB); Paul Rafferty, Westborough, MA (US); Robert Steele, Nottingham (GB); Allyson Turner, Nottingham (GB); David Wilkins, Nottingham (GB); Lee Arnold, Westborough, MA (US)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 09/689,943

(22) Filed: Oct. 12, 2000

Related U.S. Application Data

(63) Continuation-in-part of application No. 09/541,336, filed on Apr. 3, 2000.
(60) Provisional application No. 60/127,963, filed on Apr. 6, 1999.

(51) Int. Cl.[7] .......................... A61K 31/4162; A61P 1/04; C07D 495/04
(52) U.S. Cl. ................... 514/232.8; 544/140; 546/275.7; 548/311.7; 548/359.1; 548/359.5
(58) Field of Search .............................. 548/359.1, 359.5; 544/140; 514/232.8

(56) References Cited

U.S. PATENT DOCUMENTS

| | | |
|---|---|---|
| 3,843,665 | 10/1974 | Coombs et al. .................. 260/296 T |
| 3,932,430 | 1/1976 | Habeck et al. .................... 260/296 T |
| 5,397,787 | 3/1995 | Buzzetti et al. ...................... 514/300 |
| 5,593,997 | 1/1997 | Dow et al. ............................ 514/258 |

FOREIGN PATENT DOCUMENTS

| | | |
|---|---|---|
| 60-130521 | 7/1985 | (JP). |
| WO 99/17770 | 4/1999 | (WO). |
| WO 00/27822 | 5/2000 | (WO). |

OTHER PUBLICATIONS

Traxler, P.M., "Protein Tyrosine Inhibitors in Cancer Treatment," *Exp. Opin. Ther. Patents* 7(6) :571–588 (1997).

*Primary Examiner*—Robert W. Ramseur
(74) *Attorney, Agent, or Firm*—Hamilton, Brook, Smith & Reynolds, PC

(57) ABSTRACT

This invention realtes to compounds formula I

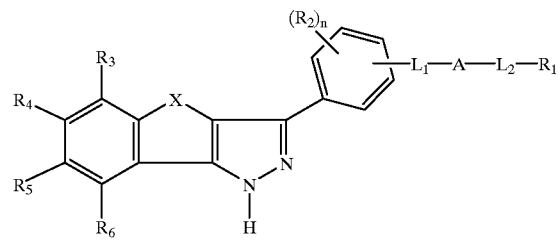

and pharmaceutically acceptable salts thereof, which are inhibitors of protein kinase activity, pharmaceutical compositions thereof and provesses for their preparation.

42 Claims, No Drawings

THERAPEUTIC AGENTS

RELATED APPLICATIONS

This application is a Continuation-in-Part of U.S. application Ser. No. 09/541,336, filed on Apr. 3, 2000, which claims the benefit of U.S. Provisional Applicatio No.: 60/127,963, filed Apr. 6, 1999, the entire teachings fo which are incorporated herein by reference.

This invention relates to certain 3-aryl pyrazoles with 4,5(3,4)-bicyclic ring fusion which are inhibitors of protein kinases particularly tyrosine kinases and serine/threonine kinases, of which some are novel compounds, to pharmaceutical compositions containnig these pyrazoles and to processes for preparing these pyrazoles.

BACKGROUND OF THE INVNEITON

There are at least 400 enzymes identified as protein kinases. These enzymes catalyze the phosphorylation of target protein substrates. The phosphorylation is usually a transfer reaction of a phosphate group from ATP to the protein substrate. The specific strcutrue in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulaiotn of cellular functions, and activation or deactivation of cellular processes. A cascade or protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases.

Protin tyrosine kinases (PTKs) are enzymes which catalyse the phosphorylation of specific tyrosine residues in cellular proteins. This post-translaiton modividaton of these substrate proteins, often enzymes themselves, acts as a molecular switch regulating cell proliferation, activation or differentiation (for review, see Schlessinger and Ulrich, 1992, Neuron 9:383–391). Aberrant or excessive PTK activity has been observed in many disease states inclduing debign and malignant proliferative disorders as well as diseases resulting from inappropriate activation of the immune system (e.g., autoimmune disorders), allograft rejection, adn fraft vs. host disease. In addition, endothelial-cell specific receptor PTKs such as KDR and Tie-2 mediate the angiogenic process, and ar e thus involved in supporting the progression of cancers adn other diseases involving inappropriate vascularization (e.g., diabetic retinopathy, choroidal neovascularization due to age-related macular degeneration, psoriasis, arthritis, infantile hemangiomas).

Tyrosine kinases can be of the receptor-type (having extracellular, transmembrane and intracellular domains) or the non-receptor type (being wholly intracellular).

Receptor Tyrosine Kinases (RTKs).

The RTKs comprise a large family of transmembrane receptors with diverse biological activities. At present, at least nineteen (19) distinct RTK subfamilies have been identified. The receptor trysone kinase (RTK) family includes receptors that are crucial for the growth and differentiation of a variety of cell types (yarden and Ullrich, Ann. Rev. Biochem. 57:433–478, 1988; Ullrich and Schlessinger, Cell 61:243–254, 1990). The intrinsic functio of RTKs is activated upon ligand binding, which results in phosphorylation of the ceceptor and multiple cellular substrats, and subsequently in a variety of cellular responses (Ullrich & Schlessinger, 1990, Cell 61:203–212). Thus, receptor tyrosine kinase mediated signal transduction is initiated by extracellular interaction with a specific grwoth factor (ligand), typcially followed by receptor dimerization, stimulation of the intrinsic protein tyrosine kinase activity and receptor trans-phosphorylation. Binding sites are thereby created for intracellular signal transduction molecules and lead to the formaiton fo complexes with a spectrum of cytoplasmic signaling molecules that facilitate the appropriate cellular response. (e.g., cell division, differentiation, metabolic effects, changes in the extracellular microenvironment) (see Schlessinger and Ullrich, 1991, Neuron 9:1–20).

Proteins with SH2 (src homology-2) or phosphoryrosine binding (PTB) domains bind activated tyrosine kinase receptors and their substrates with high affinity to propagate signals into cells. Both of the domains recognize phosphotyrosine (Fantl et al., 1992, Cell 69413–423; Songyang et al., 1994, Mol. Cell. Biol. 14:2777–2785; Songyang et al., 1993, Cell 72:767–778; Koch et al., 1991, Science 252:668–678; Shoelson, Curr. Opin. Chem. Biol. (1997), 1(2), 227–234; and Cowburn, Cur. Opin. Struct. Biol. (1997), 7(6), 835–838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, Cell 72:767–778). The specificity of the interactions between receptors or proteins and SH2 ro PTB domains of their substrates is determined by the amino acid residues immediately surroudning the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, Cell 72:767–778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which detemrines the selectivity of signaling pathways recruited by specific growth factor receptors, as well as differentaiton factor receptors.

Several receptor tyrosine kinases, and growth factos that bind thereto, have been suggested to play a role in angiogenesis, although some may promote angiogenesis indirectley (Mustonen and Alitalo, J. Cell Biol. 129:895–898, 1995). One such receptor tyrosine kinase, known as "fetal liver kinase 1" (FLK-1), is a member of the type III subclass of RTKs. an alternative designation for human FLK-1 is "kinase insert domain-containing receptor" (KDR) (Terman et al., Oncogene 6:1677–83, 1991). Another alternative designation for FLK-1/KDR is "vascular endothelial cell growth factor receptor 2" (VEGFR-2) since it binds VEGF with high affinity. The murine version of FLK-1/VEGFR-2 has also been called NYK (Oelrich et al, Oncogene 8(1):11–15, 1993). DNAs encoding mouse, rat and human FLK-1 have been isolated, and the nucleotide and encoded amino acid sequences reported (Matthews et al., Proc. Natl. Acad. Sci. USA, 88:9026–30, 1991; Terman et al., 1991, supra; Terman et al., Biochem. Biophys. Res. Comm. 187:1579–86, 1992; Sarzani et al., supra; and Millauer et al., Cell 72:835–846, 1993). Numerous studies such as those reported in Millauer et al., supra, suggest that VEGF and FLK-1/KDR/VEGFR-2 are a ligand-receptor pair that play an important role in theproliferation of vascular endothelial cells, and formation and sprouting of blood vessels, termed vasculogenesis and angiogenesis, respectively.

Antoehr type III subclass RTK designated "fms-like tyrosine kinase-1" (Flt-1) is related to FLK-1/KDR (DeVries et al. Science 255;989–991, 1992; Shibuya et al., Oncogene 5:519–524, 1990). An alternative designation fo rFlt-1 is "vascular endothelial cell growth factor receptor 1" (VEGFR-1). To date, members fo the FLK-1/KDR/VEGFR-2 and Flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, Cytokine & Growth Factor Reviews 7:259–270, 1996). Vascular endothelial cell growth factor (VEGF) binds to Flt-1 with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular devleopment. Flt-1 expression is associated with early vascualr development in mouse embryos, and with neovascularization during wound healing (Mustonen and Alitalo, supra). Expression of Flt-1 in adult organs such as kidney glomeruli suggests and additional fucniton for this receptor that is not related to cell growth (Mustonen and Alitalo, supra).

As previously stated, recent eveidence suggests that VEGF plays a role in the stimulation of both normal and pathological angiogenesis (Jakeman et al., Endocrinology 133:848–859, 1993; Kolch et al., Breast Cancer Research and Treatment 36: 139–155, 1995; Ferrara et al., Endocrine Reviews 18(1); 4–25, 1997; Ferrara et al., Regulation of Angiogenesis (ed. L. D. Goldberg and E. M. Rosen), 209–232, 1997). In addition, VEGF has been implicated in the control and enhancement of vascular permeability (Connolly, et al., J. Biol. Chem. 264: 20017–20024, 1989; Brown et al., Regulation of Angiogenesis (ed. L. D. Goldberg and E. M. Rosen), 233–269, 1997).

Different forms of VEGF arising from alternative splicing of mRNA have been reported, inlcuding the four species described by Ferrara et al. (J. Cell. Biochem. 47:211–218, 1991). Both secreted and predominantly cell-associated species of VEGF have been identified by Ferrara et al. supra, and the protein is knonw to exist in the form of disulfide linked dimers.

Several related homologs of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of thier specific functions as illustrated below (Korpelainen and Alitalo, Curr. Opin. Cell Biol., 159–164, 1998 and references cited therein).

Placenta growth factor (P1GF) has an amino acid sequence that exhibits significant homology to the VEGF sequence (Park et al., J. Biol. Chem. 269:25646–54, 1994; Maglione et al. Oncogene 8:925–31, 1993). As with VEGF, different species of P1GF arise from alternative splicing of mRNA, and the protein exists in dimeric form (Part et al., supra). P1GF-1 and P1GF-2 bind to Flt-1 with ghigh affinity, and P1GF-2 also avidly binds to neuropilin-1 (Migdal et al,J. Biol. Chem. 273(35):22272–22278), but neither binds to FLK-1/KDR (Part et al., supra). P1GF has been reported to potentiate both the vascular permeability and mitrogenic effect of VEGF on endothelial cells when VEGF is present at low concnetrations (purportedly due to heterodimer formation) (Part et al., supra).

VEGF-B is produced as two isoforms (167 and 185 residues) that also appear to bind Flt-1/VEGFR-1. It may play a role in the regulation of extracellular matrix degradation, cell adhesi9on, and migration through modulation of the expression and activity of urokinase type plasminogen activator and plasminogen activator inhibitor 1 (Pepper et al, Proc. Natl. Acad. Sci. U.S.A. (1998), 95(20):11709–11714).

VEGF-C was originally clones as a ligand for VEGFR-3/Flt-4 which is primarily expressed by lymphatic endothelial cells. In its fully processed form, VEGF-C can also bind KDR/VEGFR-2 and stimulate proliferation and migraiton of endothelial cells in vitro and angiogenesis in in vivo models (Lymboussaki et al, Am. J. Pathol. (1998), 153(2):395–403; Witzenbichler et al, Am. J. Pathol. (1998), 153(2), 381–394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, J. Biol. Chem. (1998), 273(14),8413–8418).

The most recently discovered VEGF-D is structurally very similar to VEGF-C. VEGF-D is reported to bind and activate at least tow VEGFRs, VEGFR-3/Flt-4 and KDR/VEGFR-2. It was originally cloned as a c-fos inducible mitrogen for fibroblasts and is most prominently expressed in the mesenchymal cells of the lung and skin (Achen et al, Proc. Natl. Acad. Sci. U.S.A. (1998), 95(2),548–553 and references therein).

VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

Based upon emerging discoveries of other homologs of VEGF and VEGFRs and the precedents for ligand and receptor heterodimerization, the actions of such VEGF homologs may involve formation of VEGF ligand heterodimers, and/or heterodimerization of receptors, or binding to a yet undiscovered VEGFR (Witzenbichler et al., suprs). Also, recent reports suggest neuropilin-1 (Migdal et al, supra) or VEGFR-3/Flt-4 (Witzenbichler et al., supra), or receptors other than KDR/VEGFR-2 may be responsible for the induction of vascular permeability (Stacker, S. A., Vitali, A., Domagala, T., Nice, E., and Wilks, A. F., "Angiogenesis and Cancer" Conference, Amer. Assoc. Cancer Res., January 1998, Orlando, Fla.; Willimas, Diabetelogia 40:S118–120 (1997)). Until now, no direct eveidence for the essential role of KDR in VEGF-mediated vascular hyperpermeability has been disclosed.

The Non-Receptor Tyrosine Kinases.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogene 8:2025–2031, which is incorporated herein by reference.

Many of the tyrosine kinases, whether an RTK or non-receptor tyrosone kinase, have been found to be involved in cellular signaling pathways involved in numerous pathogenic conditions, including cancer, psoriasis, and other hyperproliferative disorders or hyper-immune responses. Developmnet of Compounds to Modulate the PTKs.

In view of the surmised importance of PTKs to the control, regulation, and modualtion of cell proliferation, the diseases and disorders associated with abnormal cell proliferation, many attempts have been made to identify receptor and non-receptor tyrosine kinase "inhibitors" using a variety of approaches, inclduing the use of mutant ligands (U.S. Pat. No. 4,966,849), soluble receptors and antibodies (Application No. WO 94/10202; Kendall & thomas, 1994, Proc. Natl. Acad. Sci 90:10705–09; Kim et al., 1993, Nature 362:841–844), RNA ligands (Jellinek, et al., Biochemistry 33:10450–56; Takano, et al., 1993, Mol. Bio. Cell 4:358A; Kinsella, et al. 1992, Exp. Cell Res. 199:56–62; Wright, et al., 1992, J. Cellular Phys. 152:448–57) and tyrosine kinase inhibitors (WO 94/03427; WO 92/21660; WO 91/15495; WO 94/14808; U.S. Pat. No. 5,330,992; Mariani, et al., 1994, Proc. Am. Assoc. Cancer Res. 35:2268).

More recently, attempts have been made to identify small moleculaes which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; Expert Opin. Ther. Pat. (1998), 8(4): 475–478), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosone kinase inhibitors for use in the treatement of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. In particular, bis(indolylmaleimide) compounds have been described as inhibiting particular PKC serine/threonine kinase isoforms whose dysfunction is associated with altered vascular permeability in VEGF-related diseases (PCT WO97/40830; PCT WO97/40831).

The identificaiton of effective small compounds which specifically inhibit signal transduction by modulating the activity of receptor and non-receptor tyrosine and serine/threonine kinase to regulate and modulate abnormal or inapproapriate cell proliferation, differentiation, or metabolism is therefore desirable. In particular, the identificaiton of methods and compounds that specifically inhibit the function of a tyrosine kinase which is essential for angiogenic processes ro the formaiton of vascula r hyperpermeability leading to edema, ascites, effusions, exudates, and macromolecular extravasation and matrix deposition as well as associated disorders would be beneficial.

SUMMARY OF THE INVNETION

The present invention provides compounds of formula I

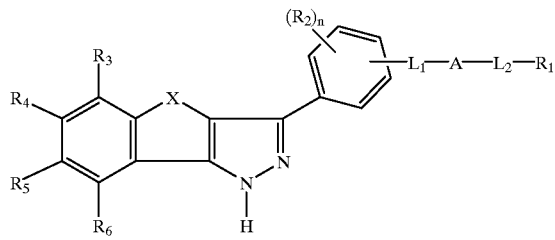

and pharmaceutically acceptable salts thereof in wihch $L_1$ represents a group of formula $(E)_s(CH_2)_q$ in which E represents $NR_{24}$, O or S, s is 0 or 1 and q is an integer from 0 to 6, provided that when s is 1 q is at least 1, in whcih the alkylene chain is optionally substituted by one or more of the following: a $C_{1-6}$ alkyl group optionally substituted by one or more hydroxy, halo or optionally substituted amino; a $C_{1-6}$ alkoxy group optionally substituted by one or more hydroxy, halo or optionally substituted amino; hydroxy; halo; or optionally substituted amino;

A represents CONH, NHCO, $SO_2NH$, $NHSO_2$, $NR_{25}$;

$L_2$ represents $C(=O)$, $C(=NH)$ or a group of formula $(CH_2)_r$ in which r is an integer from 0 to 6 in which the alkylene chain is optionally substituted by one or more of the follow: a $C_{1-6}$ alkyl group optionally substituted by one or more hydroxy, halo or optionally substituted amino; a $C_{1-6}$ alkoxy group optionally substituted by one or more hydroxy, halo or optionally substituted amino; hydroxy; halo; or optionally substituted amino;

$R_2$ for each occurrence, independently, represents a $C_{1-6}$ alkyl group optioanlly substituted by one or more of the following: halo, hydroxy, $C_{1-6}$ alkoxy or optioanlly substituted amino; a $C_{1-6}$ alkoxy group optionally substituted by one or more of the following: halo, hydroxy, $C_{1-6}$ alkoxy group optionally substituted by one or more of the following: halo, hydroxy, $C_{1-6}$ alkoxy or optioanlly substituted amino; or $R_2$ is halo, hydroxy, cyano, nitro, carbamoyl, a $C_{1-6}$ alkanoylgroup, a $(C_{1-6}$ alkoxy)carbonyl group or optionally substituted amino;

n represents 0,1,2 or 3

X represents a) substituted methylene b) carbonyl, c) oxygen, d) a group of fomrula $—C=NOR_7$ in which $R_7$ represents H or a $C_{1-6}$ alkyl group, e) a group of formula $NR_8$ in which $R_8$ represents H, an optionally substituted $C_{1-6}$ alkyl group or optionally substituted phenyl, f) a group of formula $(CH_2)_n$ in which n is 1, 2 or 3, or g) a group of formula $S(O)_p$ in whihch p is 0, 1 or 2;

$R_3$, $R_4$, $R_5$ and $R_6$ independently represent a) H, b) halo, c) a $C_{1-6}$ alkyl group optionally substituted by one or more of the following: hydroxy, a $C_{1-6}$ alkoxy group, halo or an optionally substituted amino group d) a $C_{1-6}$ alkoxy group optionally substituted by one or more of the following: hydroxy; a $C_{1-6}$ alkoxy group optionally substituted by one or more of the following: hydroxy;

a $C_{1-6}$ alkoxy group; halo; or an optionally substituted amino group provided that these groups are not attached to the carbon which is attached to the oxygen of the alkoxy group; e) optionally substituted phenoxy, f) hydroxy, g) a group formula $COR_a$ in which $R_a$ represents hydroxy, a $C_{1-6}$ alkoxy group or $R_a$ represents an optionally substituted amino group, h) an optionally substituted amino group i) a $C_{1-6}$ alkanoyl group j) nitro, k) optionally substituted phenyl $C_{1-6}$ alkyl, l) optionally substituted phenyl $C_{1-6}$ alkoxy m) cyano; or o) a $C_{2-4}$ alkenyl group or a $C_{2-4}$ alkynyl group each of which is optionally substituted by phenyl which is optionally substituted by one or more of the following: a $C_{1-6}$ alkyl group, a $C_1$ alkoxy group or halo; an d 1) when A is $SO_2NH$, or $NHSO_2$ $R_1$ represents a) optionally substituted phenyl b) optionally substituted heteroaryl, c) a five, six, seven, or eight membered saturated heterocyclic ring contianing a nitrogen atom which optionally contains an additional hetero atom selected from O, S or N and is optionally substituted by a $C_{1-6}$ alkyl group wherein said saturated ring may be attached through carbon or a hetero atom d) an optionally substituted amino group or e) a $C_1$ alkoxy group;

2) when A represents CONH or NHCO $R_1$ represents a) phenyl substituted by nitro or one or more $C_{1-6}$ alkoxy groups optionally substituted by one or more of the following: halo, hydroxy, $C_{1-6}$ alkoxy or optionally substituted amino b) optionally substituted heteroaryl or c) a five, six, seven or eight membered saturated heterocyclic ring containing a nitrogen atom which optionally contains an additional hetero atom selected from O, S or N and is optionally substituted by a $C_{1-6}$ alkyl group wherein said saturated ring is attached through a carbon atom or d) a $C_{1-6}$ alkoxy group;

3) when A represents a group $NR_{25}$ and q is at least 1 then $R_1$ represents a) optionally substituted phenyl b) optionally substituted heteroaryl or c) an optionally substituted amino group; and 4) when A represents a group $NR_{25}$ and q is 0 and s is 0 then $R_1$ represents optionally substituted heteroaryl;

$R_{24}$ and $R_{25}$ independently represnet H; a $C_{1-6}$ alkyl group optionally substituted by one or more of the following: hydroxy, a $C_{1-6}$ alkoxy group, halo or an optionally substituted amino group; a $C_{1-6}$ alkanoyl group or a $C_{1-6}$ alkylsulphonyl group;

provided that no two hetero atoms are attached to the same sp3 hybridized carbon atom.

It will be appreciated by those skilled in the art that when n is other than 0 or 1 that the groups $R_2$ may be the same or different.

The term optionally substituted amino group means a group of formula $NR_kR_1$ in whihch $R_k$ an $dr_1$ independently represent hydrogen, a $C_{1-12}$ alkyl group, a $C_{1-12}$ alkoxy group, a $C_{3-12}$ cycloalkyl group, a phenyl group, a phenyl$C_{1-6}$ alkyl group, a heteroaryl group or heteroaryl $C_{1-6}$ alkyl group wherein each of said groups is optionally substituted by one or more of the following: a $C_{1-6}$ alkyl group, a $C_{1-6}$ alkoxy group, hydroxy, halo; or $R_k$ and $R_1$ together with the nitrogen atom to which they are attached represent a five, six, seven or eight membered saturated heterocyclic ring whihc optionally contains an additional hetero atom selected from O, S or N and is optionally substituted by a $C_{1-6}$ alkyl group.

As used herein, many moieties or substituents are termed as being either "substituted or unsubstituted" or "optionally substituted". Unless otherwised specified herein, when a moiety is modified by one of these terms, it denotes that any poriton of the moiety that is known to one skilled in the art as being available for substitution can be substituted, which includes one or more substituents, where if more than one substituent then each substituent is independently selected. Such means for substitution as well-known in the art and/or taught by the instant disclosure. For purposes of exemplificaiton, which should not be construed as limiting the scope fo this invention, some examples of groups that are substituents are: alkyl groups (whihc itself can also be substituted, such as $CF_3$), alkoxy group (which itself can be substituted, such as $OCF_3$), a halogen or halo group (F, Cl, Br, I), hydroxy, nitro, oxo, CN, COH, COOH, amino, N-alkylamino or N,N-dialkylamino (in which the alkyl groups can also be substituted), esters (—C(O)—OR, where R is a groups such as alkyl, aryl, etc., which can be substituted), aryl (most preferred is phenyl, which can be substituted) and arylalkyl (which can be substituted).

The term optionally substituted as used herein with reference to phenyl and heteroaryl means substituted by one or more of the following a) halo, b) a $C_{1-6}$ alkyl group optionally substituted by one or more of the following: hydroxy, halo, an optionally substituted amino group or a five, six, seven or eight membered saturated heterocyclic ring containing a nitrogen atom which optionally contains an addiotional hetero atom selected from O, S or N and is optionally substituted by a $C_{1-6}$ alkyl group wherein said saturated ring is attached through a carbon atom, c) a $C_{1-6}$ alkoxy group optionally substituted by one or more of the following: hydroxy; a $C_{1-6}$ alkoxy group; halo; or optionally substituted amino group provided that these groups are not attached to the carbon which is attached to the oxygen of the alkoxy group, or a five, six, seven or eight membered saturated heterocyclic ring containing a nitrogen atom which optionally contains an additional hetero atom selected from O, S or N and is optionally substituted by a $C_{1-6}$ alkyl group wherein said saturated ring is attached through a carbon atom, d) optionally substituted phenoxy, e) hydroxy, f) a group formula $COR_a$ in whihc $R_a$ represents hydroxy, a $C_{1-6}$ alkoxy group or $R_a$ represents a group of formula $NR_bR_c$ in whihc $R_b$ and $R_c$ indepdently represent hydrogen, a $C_{1-12}$ alkyl group, a $C_3$ cycloalkyl group or phenyl wherein the alkyl group, the cycloalkyl group and phenyl are optionally substituted by one or more of the following: hydroxy, halo, a $C_{3-12}$ cycloalkyl group or an amino group of formula $NR_hR_j$ wherien $R_h$ and $R_j$ independently represent hydrogen or a $C_{1-6}$ alkyl group or wherein $R_h$ $R_j$ together with the nitrogen atom to which they are attached represent a five, six, seven or eight membered saturated heterocyclic ring which optionally contains an additional hetero atom selected from O, S or N and is optionally substituted by a $C_{1-6}$ alkyl group, g) a group of formula $NR_d R_e$ in which $R_d$ and $R_e$ are independently selected from hydrogen, a $C_{1-12}$ alkyl group, a $C_{3-12}$ cycloalkyl group or phenyl or a group of formula $COR_f$ wherien $R_f$ represnets hydrogne, a $C_{1-12}$ alkyl group, a $C_{3-12}$ cycloalkyl group, a phenyl $C_{1-6}$ alkyl group or phenyl wherien in eahc case the alkyl group, the cycloalkyl group and phenyl are optionally substituted by one or more fo the following: halo, hydroxy, nitro or an amino group of formula $NR_hR_j$ wherien $R_h$ and $R_j$ are as defined above, h) a group of formula $O(CH_2)_m R_g$ in which m is 2, 3, 4 or 5 $R_g$ are as defined above, h) a group of formula $NR_dR_e$ in which $R_d$ and $R_e$ are as defined above; or $R_g$ represents a group of formula $COR_a$ wherien $R_a$ is as defined above and m is 1, 2, 3, 4 or 5, i) nitro, j) optionally substituted phenyl $C_{1-6}$ alkyl, k) optionally substituted phenyl $C_{1-6}$ alkoxy, l)

cyano, m) a C$_{3-6}$alkenyloxy group, n) a pyridyloxy or pyridylthio group in which the pyridine ring is optionally substituted by one or more of the following: trifluoromethyl or nitro, o) hydroxyamidino, p) aminomethyl, q) formamidomethyl, r) a C$_{1-6}$ alkythio group, s) phenyl, and t) a C$_{2-4}$ alkenyl group or a C$_{2-4}$ alkynyl group each of which is optionally substituted by phenyl which is optionally substituted by one or more of the following: a C$_{1-6}$ alkyl group, a C$_{1-6}$ alkoxy group or halo.

The term heteroaryl means an optionally substituted mono or bicyclic aromatic heterocycle in which the heterocycle contains 1, 2, 3 or 4 heteroatoms selected from nitrogen, sulphur or oxygen. The heteroaryl group may be attached through carbon or a hetero atom. Suitable heteroaryl groups include imidazolyl, furyl, pyrrolyl, thienyl, oxazolyl, thiazolyl, isoxazolyl, thiadiazolyl, oxadiazolyl, pyridinyl, pyrimidyl, pyrazinyl, pyridazinyl, quinolyl, isoquniolyl, indazolyl, benzoxazolyl, benzofuryl, benzothiazolyl, indolizinyl, imidazopyridinyl, pyrazolyl, triazolyl, isothiazolyl, oxazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl or benzo(b)thienyl each of which is optionally substituted as described above.

when the optionally substituted amino group represents a saturated heterocyclic ring the ring is preferably morpholino, perhydrothiazin-4-yl, piperidino, pyrrolidin-1-yl, piperazin-1-yl, 4-methylpiperazin-4-yl, thiamorpholinyl, perhydro-1,4-diazepin-1-yl or perhydroazepinyl.

The term substituted methylene means for example methylene substitued by one or more of the following: hydroxy or a C$_{1-6}$ alkyl gruop wherien the alkyl group is optionally further substituted by a gorup of formula NR$_r$R$_s$ wherien R$_r$, R$_s$ independently represent H or a C$_{1-6}$ alkyl group.

It will be understood that any group mentioned herein which contains a chain of three or more atoms signifies a group in wihc the chain may be straight or branched. For example, an alkyl group may comprise propyl, which indlcuedes n-propyl and isopropyl, and butyl, which includes n-butyl, sec-butyl, isobutyl and tert-butyl. The term C$_{3-12}$ cycloalkyl group includes bridged groups for example adamantyl. The term 'halo' as used herein signifies fluoro, chloro, bromo and iodo.

Preferably X is CH$_2$ or S.

In a first group of preferred compounds of formula I, X is CH$_2$ and A is NR$_{25}$.

In a second group of preferred compounds of formula I, X is S and A is NR$_{25}$.

In a third group of preferred compounds of formula I, X is CH$_2$ and A is HNSO$_2$.

In a fourth group of preferred compounds of formula I, X is CH$_2$ and A is SO$_2$NH.

In a fifth group of preferred compounds of formula I, X is CH$_2$ and A is CONH.

In a sixth group of preferred compounds of forumla I, X is CH$_2$ and A is HNCO.

In most preferred compounds of formula I, X is CH$_2$, A is NR$_{25}$, L$_1$ is (CH$_2$)$_q$ in which q is an integer from 1 to 6 and the alkylene chain is optionally substituted by one or more of the following: a C$_{1-6}$ alkyl gruop optionally substituted by one or more hydroxy, halo or optionally substituted amino; a C$_{1-6}$ alkoxy group optionally subsituted by one or more hydroxy, halo or optionally substituted amino; hydroxy; halo; or optionally substituted amino; L$_2$ is a bond and R$_1$ is optionally substitued pyridyl.

Compounds of formula I may exist as salts with pharmaceutically acceptable acids. The present invention includes such salts. Examples of such salts include hydrochlorides, hydrobromides, sulphates, methanesulphonates, nitrates, maleates, acetates, citrates, fumarates, tartrates [eg(+)-tartrates, (−)-tartrates or mixtures thereof including racemic mixtures], succinates, benzoates and salts with amino acids such as glutamic acid. These salts may be prepared by methods known to those skilled in the art.

Certain compounds of formula I which have acidic substituents may exist as salts with pharmaceutically acceptabel bases. The present invention includes such salts. Example of such salts include sodium salts, potassium salts, lysine salts and arginine salts. These salts may be prepared by method sknown to those skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centres, and exist in different optically active forms. When compounds of formula I contain one chiral centre, the compounds exist in two enantiomeric forms and the present invention includes both enantiomerts and mixtures of enantiomers. The enantiomers may be resolved by emthods known to those skilled in the art, for example by formation of diastereoisomeric salts which may be separated, for example, by crystallization; formation of diastereoisomeric derivatives or complexes which mayt be separated, for example, by crystallization, gas-liquid or liquid chromatorgraphy; selective reaction of one enantiomer wiht an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is require to liberate the desired enantiomeric form. Alternatively, specific enantiomers may be synthesized by asymmetric synthesis using optically active reagents, substrates, catalysts or solvents, or by converting one enantiomer into the othe rby asymmetric transformation.

When a compound of formula I contains more than one chiral centre it may exist in diastereoisomeric forms. The diatereoisomeric pairs may be separated by emthods known to those skilled in the art, for example charomatography or crystallization and the individual enantiomers wihtin each pair may be separated as described above. The present inventino includes each diastereoisomer of compounds of formula I an dmixtures thereof.

Certain compounds of formula I may exist in differnt tautomeric forms or as differnt geometric isomers, and the present ivnention includes each tautomer and/or geometric isomer of compounds of formula I and mixtures thereof.

Certain compounds of formula I may exist in different stable conformational forms which may be separabl. Torsional asymmetry due to restricted rotaiton about an asymmetric single bond, for example because of steri chindrance or ring strain, may permit separation of different conformers. The present invention includes each conformational isomer of compounds of formula I and mixtures thereof.

Certain compounds of formula I may exist in zwitterionic form and the present invnetion includes each zwitterionic form of compounds of formula I and mixtures thereof.

The compounds of this invention are useful as inhibitors of serine/threonine and tyrosine kinases. In particular, the compounds of this invention are useful as inhibitors of tyrosine kinases that are important in hyperproliferative diseases, especially in the process of angiogenesis. Since these compounds are anti-angiogenic, they are important substances for inhibiting the progression of disease states where angiogenesis is an important component.

Preferred definitions of the substituents are now given.

Preferably $R_1$ represents optionally substituted phenyl, optionally substituted thienyl, optionally substituted pyridyl, optionally substituted furyl, or optionally substituted pyrrolyl.

More preferably $R_1$ represents 2-thienyl, 3-thienyl, 2-furyl, 3-furyl, 2-pyridyl, 3-pyridyl or 4-pyridyl each of which is optionally subsituted, and optionally mono-, di- and tri-substitued phenyl, wherein the substituents are selected from optionally subsituted alkoxy (particularly methoxy, a $C_{1-6}$ alkoxy which is optionally substituted with an amine represented by the formula $NR_{28}R_{29}$, or a five, six, seven or eight membered saturated heterocyclic group containing a nitrogen and which optionally contains one or more hetero atoms independently selected from N, O and S,3-morpholinopropoxy, 2-morpholinoethyoxy, 3-carboxypropxy, carboxymethoxy, 2-carboxyethyoxy, 2-carbamoylethoxy, carbamoylmethoxy, 3-carbamoylpropoxy, 2-piperidinoethoxy, 2-(piperazin-1-yl)ethoxy, 2-(pyrrolidin-1yl)ethoxy, 2-dimethylaminoethoxy, 2-(perhydro-thiazin-4-yl)ethoxy, 3-piperidinopropoxy, 3-(piperazin-1-yl)propoxy, 3-(pyrrolidin-1yl)-propoxy, 3-dimethylaminopropoxy, 3-(perhydrothiazin-4-yl) propoxy), lower alkyl (particularly methyl or a C1-6 alkyl which is optionally substituted wiht an amine represented by the formula $NR_{28}R_{29}$, or a five, six, seven or eight membered saturated heterocyclic group containg a nitrogen and which optionally contains one or more hetero atoms independently selected from N, O and S.), halo (particularly fluoro and chloro), aryl (particularly phenyl), hyroxy, aryloxy (particualrly phenoxy), arylalkoxy (particularly benzyloxy), di-lower-alkylamino (particuarly diemthylamino), polyhaol-lower-alkyl, polyhalo-loweralkoxy (particularly difluoromethoxy), nitro, cyano, loweralkylthio (particularly methylthio), carboxy, loweralkoxycarbonyl (particularly methoxycarbonyl), amino (particularly a mono- or di-lower alkyl amino), amido (particuarly acetamido and benzamido) and optionally substituted carbamoyl (particularly carbamoyl, N-methycarbamoyl, N-phenylcarbamoyl) and a pyridyloxy or pyridylthio group in which the pyridine ring is optionally substituted by one or more of the following: trifluoromethyl or nitro.

Most preferably $R_1$ represnets 4-pyridyl, 2-formamidomethyl-4-pyridyl, 2-aminomethyl-4-pyridyl, 2-(hydroxyamidino)-4-pyridyl, 2-carbamoyl-4-pyridyl, 4-pyridyl-N-oxide, 2-chloro-4-pyridyl, 2-cyano-4-pyridyl, 5-methyl-2-methyl-2-furyl, 5-(2-nitro-4-trifluoromethylphenyl)fur-2-yl, phenyl, 4-methoxyphenyl, 3-methoxyphenyl, 2-methoxyphenyl, 3,4-dimethoxyphenyl, 3,4,5-trimethoxyphenyl, 4-(3-morpholino-propoxy)phenyl, 4-(2-morpholinoethoxy)phenyl, 4-(3-carboxypropoxy)phenyl, 4-carboxymethoxyphenyl, 4-(3-carbamoylpropoxy)phenyl, 4-carbamoylmethoxyphenyl, 3-(3-morpholino-propoxy)phenyl, 3-(2-morpholinoethoxy)phenyl, 3-(3-carboxy-propoxy)phenyl, 4-carboxymethoxyphenyl, 3-(3-carbamoylpropxy)phenyl, 3-carbamoylmethoxyphenyl, 2-hydroxyphenyl, 3-hydroxyphenyl, 4-hydroxyphenyl, 3-hydroxy-4-methoxyphenyl, 4-hydroxy-3-methoxyphenyl, 4-difluoromethoxyphenyl, 3-nitrophenyl, 4-nitrophenyl, 3,5-di-tert-butyl-4-hydroxyphenyl, 4-methylphenyl, 4-fluorophenyl, 2-chlorophenyl, 3-chlorophenyl, 4-chlorophenyl, 2,4-dichlorophenyl, 2-chloro-5-nitrophenyl, 4-fluoro-2-chlorophenyl, 4-methyltiophenyl, 4-biphenylyl, 3-phenoxyphenyl, 4-phenoxyphenyl, 4-benzyloxyphenyl, 4-dimethylaminopheny, 4-diethylaminophenyl, 4-methoxycarbonylphenyl, 4-carbamoylphenyl, 4-cyanophenyl, 4-N-methylcarbamoylpheny, 4-N-phenylcarbamoylphenyl, 4-acetamidophenyl, 4-benzamidophenyl, 4-carboxyphenyl, 4-[N-(2-diethylaminoethyl)carbamoyl]phenyl, 4-(prop-1-enyloxy)phenyl, 3-(2-hydroxyethoxy)phenyl, 3-(N-(2-diethyl aminoethyl)-carbamoylmethoxy)phenyl, 3-[3-(N-(2-diethylaminoethyl)carbamoyl)propoxy]phenyl, 4-(N-(2-diethylaminoethyl)carbamoylmethoxy)phenyl, 4-[3-(N-(2-diethylaminoethyl)-carbamoyl)propoxy]phenyl, 2-furyl, 5-[3,5-bis(trifluoromethyl)phenyl]-2-furyl, 3-bromo-2-thienyl, 5-methoxy-2-furyl, 5(2-nitro-4-trifluoromethylphenyl)-2-furyl, 3-N-(2-morpholinoethyl) carbamoylmethoxy)phenyl, 3-[3-(N-(2-morpholinoethyl) carbamoyl)-propoxyphenyl], 4(N-(2-morpholinoethyl)-carbamoylmethoxy)phenyl, 4-(morpholinoacetamido) phenyl and 4-[3-(N-(2-morpholinoethyl)carbamoyl) propoxy]-phenyl.

Preferably $R_3$, $R_4$, $R_5$ and $R_6$ independently represent hydrogen, halo (particualrly fluoro), optionally substituted lower alkoxy (particularly methoxy, 3-morpholinopropoxy, 2-morpholinoethoxy, 3-carboxypropoxy, carboxymethoxy, 2-carboxyethoxy, 2-carbamoylethoxy, 3-carbamoylpropoxy, 2-piperidinoethyoxy, 2-(piperazin-1-yl)ethoxy, 2-(pyrrolidin-1-yl)ethoxy, 2-dimethylaminoethoxy, 2-(perhydrothiazin-1-yl)ethoxy, 3-piperidinopropoxy, 3-(piperazin-1-yl)propoxy, 3-(pyrrolidin-1-yl)propoxy, 3-dimethylaminopropoxy, 3(perhydrothiazin-4-yl)propoxy), carbamoylmethoxy, hydroxypropyloxy, hydroxyethoxy, (3-morpholino)propoxy and 2-morpholino)ethoxy), amido (particularly acetamido and benzamido), optionally substituted carbamoyl (particularly carbamoyl, N-methylcarbamoyl and N-phenylcarbamoyl), carboxy, nitro and amino.

More preferably, $R_3$, $R_4$, $R_5$ and $R_6$ represent the following: 6,7-dimethoxy, 6,7,8-trimethoxy, 6-fluoro, 6-acetamido, 7-methoxy, 6-carbamoyl, 6-(N-methyl-carbamoyl), 6-(N-phenylcarbamoyl), (3-morpholino)propoxy and 2-morpholino)-ethoxy.

In one embodiment, compounds of the invention can be represented by formula Ia:

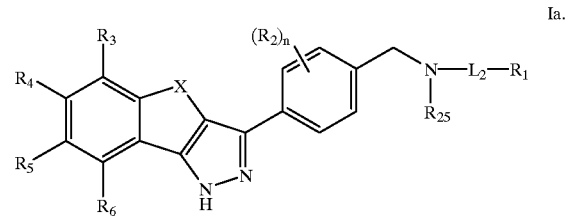

Ia.

and pharmaceutically acceptable salts thereof, wherein:
$R_2$, $R_3$, $R_4$, $R_5$, $R_6$, and n are defined as in formula I;
X is limited to a) methylene which is optionally substituted with a $C_{1-6}$ alkyl group, b) carbonyl, c) oxygen, d) a group of formula —C=$NOR_7$ in which $R_7$ represents H or a $C_{1-6}$ alkyl group, e) a group of formula $NR_8$ in which $R_8$ represents H, an optionally substituted $C_{1-6}$ alkyl group or optionally substituted phenyl, or f) a group of formula $S(O)_p$ in which p is 0, 1 or 2;
$L_2$ is limited to a single bond, C(=O), C(=NH), or a $C_{1-6}$ alkyl group;

$R_{25}$ is limited to H, a $C_{1-6}$ alkyl or a $C_{1-6}$ alkanoyl; and $R_1$ is limited to an optionally substituted phenyl, an optionally substituted heteroaryl, or an optionally substituted amino group.

In another embodiment, compounds of the invention can be represented by formula Ib:

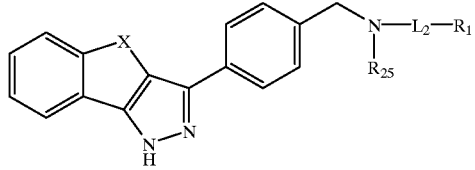

Ib.

and pharmaceutically acceptable salts thereof, wherein:

X is limited to a) a methylene which is optionally substituted with a $C_{1-6}$ alkyl, b) carbonyl, c) oxygen, or d) a group of formula $S(O)_p$, wherein p is 0, 1, or 2;

$L_2$ is limited to a single bond, C(=O), C(=NH), or a $C_{1-6}$ alkyl group;

$R_{25}$ is limited to H, a $C_{1-6}$ alkyl or a $C_{1-6}$ alkanoyl; and $R_1$ is limited to an optionally substituted phenyl, an optionally substituted heteroaryl, or an optionally substituted amino group.

In another embodiment, $R_1$ is pyridyl and compounds of the invention are represented by formula Ic:

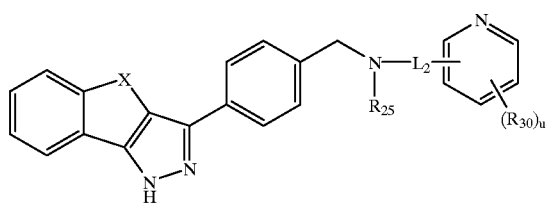

Ic.

and pharmaceutically acceptable salts thereof, wherein:

u is 0, 1, 2, 3, or 4;

X is limited to a) a methylene which is optionally substituted with a $C_{1-6}$ alkyl, b) carbonyl, c) oxygen, or d) a group of formula $S(O)_p$, wherein p is a 0, 1, or 2;

$L_2$ is limited to a single bond, C(=O), C(=NH), or a $C_{1-6}$ alkyl group;

$R_{25}$ is limited to H, a $C_{1-6}$ alkyl or a $C_{1-6}$ alkanoyl;

$R_{30}$ for each occurrence, independently, represents a) an amine which is optionally mono- or disubstituted with an independently selected $C_{1-6}$ alkyl, b) a $C_{1-6}$ alkoxy which is optionally substituted with an amine represented by the formula $NR_{28}R_{29}$, or a five, six, seven or eight membered saturated heterocyclic group containing a nitrogen and which optionally contains one or more hetero atoms independently selected from N, O and S, c) a halo, d) hydroxy, or e) a $C_{1-6}$ alkyl which is optionally substituted with an amine represented by the formula $NR_{28}R_{29}$, or a five, six, seven, or eight membered saturated heterocyclic group containing a nitrogen and which optionally contains one or more hetero atoms independently selected from N, O and S; and $R_{28}$ and $R_{29}$ for each occurrence, independently, represents H or a $C_{1-6}$ alkyl.

In one embodiment, u is limited to 1, 2, 3, or 4.

Preferably, $R_{30}$ is selected from the group consisting of dimethylamino, diethylamino, methyl, hydroxy, chloro, and methoxy.

In another embodiment, compounds of the invention can be represented by formula Id:

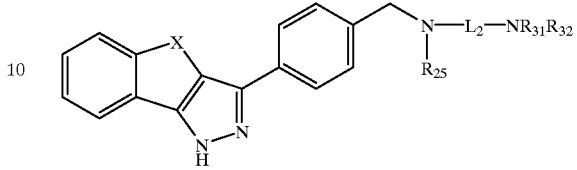

Id.

and pharmaceutically acceptable salts thereof, wherein:

X is limited to a) a methylene which is optionally substituted with a $C_{1-6}$ alkyl, b) carbonyl, c) oxygen, or d) a group of formula $S(O)_p$, wherein p is 0, 1, or 2;

$L_2$ is limited to a single bond, C(=O), C(=NH), or a $C_{1-6}$ alkyl group;

$R_{25}$ is limited to H, a $C_{1-6}$ alkyl or a $C_{1-6}$ alkanoyl;

$R_{31}$ and $R_{32}$ are each, independently, H or a $C_{1-6}$ alkyl which is optionally substituted with one or more groups independently selected from a) an amine represented by the formula $NR_{28}R_{29}$, b) a $C_{1-6}$ alkoxy which is optionally substituted with a five, six, seven or eight membered heterocyclic group containing one or more hetero atoms independently selected from N, O and S or an amine represented by the formula $NR_{28}R_{29}$, c) a halo, d) hydroxy; e) a $C_{1-6}$ alkyl, or f) a five, six, seven or eight membered heterocyclic group containing one or more hetero atoms independently selected from N, O, and S; and $R_{28}$ and $R_{29}$ are defined as above.

In a preferred embodiment $R_{31}$ and $R_{32}$ are each, independently, H or an unsubstituted $C_{1-6}$ alkyl and $L_2$ is a $C_{2-5}$ alkyl.

In formulas Ia, Ib, Ic and Id, X is, preferably, S or $CH_2$ and $R_{25}$ is H.

The term lower as used herein means a group having 1 to 6 carbon atoms.

Specific compounds of the present invention include:

4-(1,4-dihydroindeno[1,2-c]pyrazole)-N-(4-pyridyl)benzylamine;

N-[4-(1,4-dihydroindeno[1,2-c]pyrazol-3-yl)phenyl]benzenesulphonamide;

4-(1,4-dihydroindeno[1,2-c]pyrazol-3yl)-N-(2-methoxyethyl)benzamide;

4-(1,4-dihydroindeno[1,2-c]pyrazol-3-yl)-N-(4-nitrophenyl)benzamide;

4-(1,4-dihydroindeno[1,2-c]pyrazol-3-yl)imidazol-1-ylacetanilide;

4-(1,4-dihydroindeno[1,2-c]pyrazol-3-yl)-N-[2-(imidazol-1-yl)ethyl]aniline;

4-(1,4-dihydroindeno[1,2-c]pyrazol-3-yl)-N-(2-morpholinoethyl)benzenesulphonamide;

4-(1,4-dihydroindeno[1,2-c]pyrazol-3-yl)-N-(2-methoxyethyl)benzenesulphonamide;

N-[2-(N,N-diethylamino)ethyl]-4-(1,4-dihydroindeno[1,2-c]pyrazol-3-yl)benzylamine;

N-[2-(N,N-diethylamino)ethyl]-4-(1,4-dihydroindeno[1,2-c]pyrazol-3-yl)benzenesulphonamide;

4-(1,4-dihydroindeno[1,2-c]pyrazol-3-yl)-N-(2-morpholinoethyl)benzylamine;

N-(4-ethoxyphenyl)-4-(1,4-dihydroindeno[1,2-c]pyrazol-3-yl)benzylamine;

(S)-4-(1,4-dihydroindeno[1,2-c]pyrazol-3-yl)-N-(pyrrolidin-2-ylmethyl)benzamide;
4-(1H-[1]benzothieno[3,2-c]pyrazol-3-yl)-N-[3-(imidazol-1-yl)propyl]benzylamine;
4-(1H-[1]benzothieno[3,2-c]pyrazol-3-yl)-N-(2-morpholinoethyl)benzylamine;
and pharmaceutically acceptable salts thereof including individual enantiomers and mixture of enantiomers.

Another specific group of compounds of the invention includes:
[4-(1H-benzo[4,5]-thieno[3,2-c]pyrazol-3-yl)-benzyl]-(2-pyridin-4-yl-ethyl)-amine;
$N^5$-[4-(1H-benzo[4,5]thieno[3,2-c]pyrazol-3-yl)-benzyl]-$N^2,N^2$-diethyl-pyridine-2,5-diamine;
N-[4(4,4-dimethyl-1,4-dihydro-indeno[1,2-c]pyrazol-3-yl)benzyl]-N,N-dimethyl-ethane-1,2-diamine;
[4-(4-oxo-1,4-dihydro-4$\lambda^4$-benzo[4,5]thieno[3,2-c]pyrazol-3-yl)-benzyl]pyridin-4-yl-amine;
[4-(4,4-dioxo-1,4-dihydro-4$\lambda^6$-benzo[4,5]thieno[3,2-c]pyrazol-3-yl)-benzyl]pyridin-4-yl-amine;
[4-(1H-benzo[4,5]thieno[3,2-c]pyrazol-3-yl)-benzyl]-pyridin-4-yl-amine;
[4-(1,4-dihydro-indeno[1,2-c]pyrazol-3-yl)-benzyl]-pyridin-4-yl-amine;
3-[4-(pyridin-4-ylaminomethyl)-phenyl]-1H-indeno[1,2-c]pyrazol-4-one;
[4-(3H-8-oxa-2,3-diaza-cyclopenta[a]inden-1-yl)-benzyl]-pyridin-4-yl-amine;
[4-(1H-benzo[4,5]thieno[3,2-c]pyrazol-3-yl)benzyl]-pyridin-3-yl-amine;
[4-(1H-benzo[4,5]thieno[3,2-c]pyrazol-3-yl)benzyl]-pyridin-2-yl-amine;
[4-(1H-benzo[4,5]thieno[3,2-c]pyrazol-3-yl)benzyl]-pyridin-4methyl-amine;
[4-(1H-benzo[4,5]thieno[3,2-c]pyrazol-3-yl)benzyl]-(4-methyl-pyridin-2-yl)-amine;
[4-(1H-benzo[4,5]thieno[3,2-c]pyrazol-3-yl)benzyl]-(4,6-dimethyl-pyridin-2-yl)-amine;
[4-(1H-benzo[4,5]-thieno[3,2-c]pyrazol-3-yl)benzyl]-(6-methyl-pyridin-2-yl)-amine;
2-[4-(1H-benzo[4,5]thieno[3,2-c]pyrazol-3-yl)benzylamino]-pyridin-3-ol;
[4-(1H-benzo[4,5]thieno[3,2-c]pyrazol-3-yl)-benzyl]-(6-chloro-pyridin-3-yl)-amine;
$N^5$-[4-(1H-benzo[4,5]thieno[3,2-c]pyrazol-3-yl)-benzyl]-$N^2,N^2$-diethyl-pyridine-2,5-diamine;
$N^3$-[4-(1H-benzo[4,5]thieno[3,2-c]pyrazol-3-yl)-benzyl]-$N^2,N^2$-diethyl-pyridine-2,3-diamine;
$N^5$-[4-(1,4-dihydro-indeno[1,2-c]pyrazol-3-yl)-benzyl]-$N^2$,$N^2$-diethyl-pyridine-2,5-diamine;
$N^3$-[4-(1,4-dihydro-indeno[1,2-c]pyrazol-3-yl)-benzyl]-$N^2$,$N^2$-diethyl-pyridine-2,3-diamine;
[4-(1,4-dihydro-indeno[1,2-c]pyrazol-3-yl)-benzyl]-(2-methoxy-pyridin-3-yl)-amine;
[4-(1H-benzo[4,5]thieno[3,2-c]pyrazol-3-yl)-benzyl]-(4-methoxy-phenyl)-amine;
N-[4-(1,4-dihydro-indeno[1,2-c]pyrazol-3-yl)-benzyl]-N,N-dimethyl-propane-1,3-diamine;
N-[4-(1H-benzo[4,5]thieno[3,2-c]pyrazol-3-yl)-benzyl]-N-dimethyl-propane-1,3-diamine;
N-[4-(1H-benzo[4,5]thieno[3,2-c]pyrazol-3-yl)-benzyl]-N-(3-dimethylamino-propyl)-acetamide;
N-[4-(1H-benzo[4,5]thieno[3,2-c]pyrazol-3-yl)-benzyl]-N,N,N-trimethyl-propane-1,3-diamine;
N-[4-(1H-benzo[4,5]thieno[3,2-c]pyrazol-3-yl)-benzyl]-N,N,N-trimethyl-ethane-1,2-diamine;
N-[4-(1,4-dihydro-indeno[1,2-c]pyrazol-3-yl)-benzyl]-N,N,N-trimethyl-ethane-1,2-diamine;
[4-(1H-benzo[4,5]thieno[3,2-c]pyrazol-3-yl)-benzyl]-methyl-pyridin-4-yl-amine;
[4-(1H-benzo[4,5]thieno[3,2-c]pyrazol-3-yl)-benzyl]-[6-(2-dimethylamino-ethoxy)-pyridin-3-yl]-amine;
[4-(1H-benzo[4,5]thieno[3,2-c]pyrazol-3-yl)-benzyl]-[6-(2-morpholin-4-yl-ethoxy)-pyridin-3-yl]-amine; and
N-[4-(1H-benzo[4,5]thieno[3,2-c]pyrazol-3-yl)-benzyl]-N,N-dimethyl-pentane-1,5-diamine;
[4-(1,4-dihydro-indeno[1,2-c]pyrazol-3-yl)-benzyl]-[2-(4-methyl-piperazin-1-yl)-pyridin-4-yl]-amine;
[4-(1,4-dihydro-indeno[1,2-c]pyrazol-3-yl)-benzyl]-(2-morpholin-4-yl-pyridin-4-yl)-amine;
$N^4$-[4-(1,4-dihydro-indeno[1,2-c]pyrazol-3-yl)-benzyl]-$N^2$-(2-dimethylamino-ethyl)-pyridine-2,4-diamine;
N-[4-(1H-benzo[4,5]thieno[3,2-c]pyrazol-3-yl)-benzyl]-N,N-dimethyl-butane-1,4-diamine;
[4-(1H-benzo[4,5]thieno[3,2-c]pyrazol-3-yl)-benzyl]-[2-(4-methyl-piperazin-1-yl)-pyridin-4-yl]-amine;
[4-(1H-benzo[4,5]thieno[3,2-c]pyrazol-3-yl)-benzyl]-(2-morpholin-4-yl-pyridin-4-yl)-amine;
N-[4-(1,4-dihydro-indeno[1,2-c]pyrazol-3-yl)-benzyl]-isonicotinamide;
3-[4-(1,4-dihydro-indeno[1,2-c]pyrazol-3-yl)-benzyl]-1,1-dimethyl-urea;
N-[4-(1,4-dihydro-indeno[1,2-c]pyrazol-3-yl)-benzyl]-guanidine;
and pharmaceutically acceptable salts thereof including individual enantiomers and mixture of enantiomers.

The present invention provides a method of inhibiting the kinase activity of tyrosine kinases and serine/threonine kinases comprising the administration of a compound represented by formula I to said kinase in sufficient concentration to inhibit the enzyme activity of said kinase.

The present invention further includes the use of these compounds in pharmaceutical compositions with a pharmaceutically effective amount of the above-described compounds and a pharmaceutically acceptable carrier or excipient. These pharmaceutical compositions can be administered to individuals to slow or halt the process of angiogenesis in angiogenesis-aided diseases, or to treat edema, effusions, exudates, or ascites and other conditions associated with vascular hyperpermeability.

DETAILED DESCRIPTION OF THE INVENTION

The compounds of this invention have antiangiogenic properties. These antiangiogenic properties are due at least in part to the inhibition of protein tyrosine kinases essential for angiogenic processes. For this reason, these compounds can be used as active agents against such disease states as arthritis, artherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or age-related macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome)) since such diseases require a proliferation of blood vessel cells for growth and/or metastasis.

Further, some of these compounds can be used as active agents against burns, keloid, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

Therefore, the following conditions can be treated with compounds of the invention: a cancer rheumatoid arthritis, atherosclerosis, psoriasis, hemangioma, myocardial angiogenesis, coronary and cerebral collateral vascularization, ischemia, corneal disease, rubeosis, neovascular glaucoma, macular degeneration, retinopathy of prematurity, wound healing, ulcer Helicobacter related diseases, fractures, endometriosis, a diabetic condition, cat scratch fever, thyroid hyperplasia, asthma or endema following burns, trauma, chronic lung disease, stroke, polyps, cysts, synovitis, chronic and allergic inflammation, ovarian hyperstimulation syndrome, pulmonary and cerebral edema, keloid, fibrosis, cirrhosis, carpal tunnel syndrome, adult respiratory distress syndrome, ascites, an ocular condition, a cardiovascular condition. Crow-Fukase (POEMS) syndrome, sickle cell anaemia, systemic lupus, glomerulonephritis, synovitis, inflammatory bowel disease, Crohn's disease, glomerulonephritis, osteoarthritis, multiple sclerosis, graft rejection, Lyme disease, sepsis, von Hippel Lindau disease, pemphigoid, Paget's disease, polycystic kidney disease, sarcoidosis, thyroiditis, hyperviscosity syndrom, Osler-Weber-Rendu disease, chronic occlusive pulmonary disease, radiation, hypoxia, preeclampsia, menometrorrhagia, endometriosis, infection by Herpes simplex, Herpes Zoster, human immunodeficiency virus, parapoxvirus, protozoa, toxoplasmosis, and tumor-associated effusions and edema.

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEFG/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

It is envisaged that the disorders listed above are mediated to a significant extent by protein tyrosine kinase activity involving the KDR/VEGFR-2 and/or the Flt-1/VEGFR-1 tyrosine kinases. By inhibiting the activity of these tyrosine kinases, the progression of the listed disorders is inhibited because the angiogenic or vascular hyperpermeability component of the disease state is severely curtailed. The action of the compounds of this invention, by their selectivity for specific tyrosine kinases, result in a minimization of side effects that would occur if less selective tyrosine kinase inhibitors were used.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1/VEGFR-2, FGFR-1, PDGFRβ, PDGFRα, IGF-1R, c-Met, flt-1, Flt-4 TIE-2, TIE-1 Lck, Src, fyn, Lyn, Blk, Hck, fgr and yes tyrosine kinases. Certain compounds of this invention also inhibit the activity of additional tyrosine kinases such as Flt-1/VEGFR-1, Src-subfamily kinases such as Lck, Src, fyn, yes, etc. Additionally, some compounds of this invention significantly inhibit serine/threonine kinases such as CDKs which play an essential role in cell-cycle progression. The potency and specificity of the generic compounds of this invention towards a particular protein kinase can often be altered and optimized by variations in the nature, number and arrangement of the substituents (i.e., $R_1$, $R_2$, $R_3$, $R_4$, $R_5$ and $R_6$) of and conformational restrictions. In addition the metabolites of certain compounds may also possess significant protein kinases inhibitory activity.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D, or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., *Cancer Res.* 58:1278–1284 (1998) and references therein), hyperpermeability, as well as associated extravasation, subsequent edema formation and matrix deposition, and angiogenic responses, may be inhibited and minimized.

One group of preferred compounds of this invention has the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Since Flt-1 tyrosine kinase activity may mediate important events in endothelial maintenance and vascular function, an inhibition of this enzyme activity may lead to toxic or adverse effects. At the very least, such inhibition is unnecessary for blocking the angiogenic responses, induction of vascular hyperpermeability and the formation of edema, so it is wasteful and of no value to the individual. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. The preferred compounds of this invention are, therefore, selective in their tyrosine kinase inhibitory activity.

The compounds of the present invention are also useful in the treatment of ulcers—bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anaemia, Lyme's disease, pemphigoid, Paget's disease, hyperviscosity syndrome, Osler-Weber-Rendu disease, chronic inflammation, chronic occlusive pulmonary disease, asthma, rheumatoid arthritis and osteoarthritis.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukaemia and lymphoma, tumor-induced pleural or pericardial effusions, and malignant ascites.

The compounds of the present invention are also useful in the treatment of diabetic conditions such as glaucoma, diabetic retinopathy and microangiopathy.

It is envisaged that the disorders listed above are mediated to a significant extent by protein tyrosine kinase activity involving the VEGF receptors (e.g. KDR and Flt-1). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect the present invention provides compounds of formula I as defined initially above (including the provisos) for use as medicaments, particularly as inhibitors of protein kinase activity for example tyrosine kinase activity, serine kinase activity and threonine kinase activity. In yet another aspect of the present invention provides the use of compounds of formula I as defined initially above (including the provisos) in the manufacture of a medicament for use in the inhibition of protein kinase activity.

In this invention, the following definitions are applicable:

"Pharmaceutically acceptable salts" refers to those salts which retain the biological effectiveness and properties of the free bases and which are obtained by reaction with inorganic acids such as hydrochloric acid, hydrobromic acid, sulfuric acid, nitric acid, phosphoric acid or organic acids such as sulfonic acid, carboxylic acid, organic phosphoric acid, methanesulfonic acid, ethanesulfonic acid, p-toluenesulfonic acid, salicyclic acid, lactic acid, tartaric acid and the like.

"Alkyl" refers to a saturated aliphatic hydrocarbon, including straight-chain and branched-chain groups having 1 to 4 carbons.

"Alkoxy" refers to an "O-alkyl" group, where "alkyl" is defined as described above.

Pharmaceutical Formulations

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds will pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol and dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g. bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the organic molecule compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50–90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack of dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF, attenuate intracellular responses to VEGF, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include but are not limited to anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, PKC inhibitors and PI3 kinase inhibitors. The compounds of the invention and the additional pharmaceutical agents act either additively or synergistically. Thus, the administration of such a combination of substances that inhibit vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are anticipated.

The present invention also comprises the use of a compound of formula I as a medicament.

Both the Src and Syk families of kinases play pivotal roles in the regulation of immune function. The Src family currently includes Fyn, Lck, Fgr, Fes, Lyn, Src, Yes, Hck, and Blk. The Syk family is currently understood to include only Zap and Syk. The Janus family of kinases is involved in the transduction of growth factor and pro-inflammatory cytokine signals through a number of receptors. Although BTK and ITK, members of the Tec family of kinases, play a less well understood role in immunobiology, their modulation by an inhibitor may prove therapeutically beneficial. The kinases RIP, IRAK-1, IRAK-2, NIK, IKK-1 and IKK-2 are involved in the signal transduction pathways for the key pro-inflammatory cytokines TNF and IL-1. By virtue of their ability to inhibit one or more of these kinases, compounds of formula I may function as immunomodulatory agents useful for the maintenance of allografts and the treatment of autoimmune disorders. Through their ability to regulate T cell activation or the potentiation of an inflammatory process, these compounds could be used to treat such autoimmune diseases. Transplants due to rejection phenomena, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formula I, through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes. Chromosome breakage (at the ltk kinase break point on chromosome 5), translocation as in the case of the Ab1 gene with BCR (Philadelphia chromosome), truncation in instances such as c-Kit or EGFR, of mutation (e.g., Met) result in the creation of dysregulated proteins converting them from protooncogene to oncogene products. In other tumors, oncogenesis is driven by an autocrine or paracrine ligand/growth factor receptor interactions. Members of the scr-family kinases are typically involved in downstream signal transduction thereby potentiating the oncogenesis and themselves may become oncogenic by over-expression or mutation. By inhibiting the protein kinase activity of these proteins the disease process may be disrupted. Vascular restenosis may involve process of FGF and/or PDGF—promoted smooth muscle and endothelial cell proliferation. Inhibition of FGFr or PDGFr kinase activity may be an efficacious strategy for inhibiting this phenomenon. Thus compounds of formula I which inhibit the kinase activity of normal or aberrant c-kit, c-met, c-fms, src-family members, EGFr, erbB2, erbB4, BCR-Abl, PDGFr, FGFr, and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Tie-2/Tek and Tie) are essential for the stimulation of endothelial cell growth, migration, organization, differentiation and the establishment of the requisite new functional vasculature.

As a result of "vascular permeability factor" activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema, and organ dysfunction following trauma, burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF-C and VEGF-D, and HIV-Tat protein can also cause a vascular hyperpermeability response through the stimulation of a VEGFR kinase.

Tie-2 is expressed also in a select population of hematopoietic stem cells in which it may play a role in their recruitment, adhesion, regulation and differentiation (*Blood* 89, 4317–4326 (1997)); this Tie-2 expressing population may serve as circulating angiogenic endothelial progenitors. Certain agents according to formula I capable of blocking the kinase activity of endothelial cell specific kinases could therefore inhibit disease progression involving these situations.

The compounds of formula I or a salt thereof or pharmaceutical compositions containing a therapeutically effective amount thereof may be used in the treatment of benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, myasthenia gravis and systemic lupus erythematosus; psoriasis, organ transplant rejection (eg. kidney rejection, graft versus host disease), benign and neoplastic proliferative diseases, human cancers such as lung, breast, stomach, bladder, colon, pancreas, ovarian, prostate and rectal cancer and hematopoietic cells (leukemia and lymphoma), and diseases involving inappropriate vascularization for example diabetic retinopathy, choroidal neovascularization due to age-related macular degeneration, and infantile hemangiomas in human beings. In addition, such inhibitors may be useful in the treatment of disorders involving VEGF mediated edema, ascites, effusions, and exudates, including for example, macular edema, cerebral edema, and adult respiratory distress syndrome (ARDS).

The compounds of the present invention may also be useful in the prophylaxis of the above diseases.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., Nature, 375:536–539) by a test compound relative to control.

KDR Tyrosine Kinase Production Using Baculovirus System:

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6KDR(aa789-1354)$ were lysed by adding 50 ml of Triton X-100 lysis buffer (20 mM Tris, pH 8.0, 137 mM NaCl, 10% glycerol, 1% Triton X-100, 1 mM PMSF, 10 µg/ml aprotinin, 1 µg/ml leupeptin) to the cell pellet from 1 L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

Human Tie-2 Kinase Production and Purification

The coding sequence for the human Tie-2 intra-cellular domain (aa775-1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at $2 \times 10^6$/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786–1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat #E-3641); 500 units/50 µl) and the EGF ligand was acquired from Oncogene Research Products/Calbiochem (Cat #PF011-100).

Expression of ZAP70

The baculoviral expression vector used was pVL1393. (Pharmingen, Los Angeles, Calif.) The nucleotide sequence encoding amino acids $M(H)6LVPR_9S$ was placed 5' to the region encoding the entirety of ZAP70 (amino acids 1–619). The nucleotide sequence encoding the ZAP70 coding region was generated through PCR using cDNA libraries isolated from Jurkat immortalized T-cells. The histidine residues enabled affinity purification of the protein (vide infra). The $LVPR_9S$ bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and purification of ZAP70

SF-9 cells were lysed in a buffer consisting of 20 mM Tris, pH 8.0, 137 mM NaCl, 10% glycerol, 1% Triton X-100, 1 mM PMSF, 1 µg/ml leupeptin, 10 µg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Lck source

Lck or truncated forms of Lck may be commercially obtained (e.g. from Upstate Biotechnology Inc. (Saranac Lake, N.Y.) and Santa Cruz Biotechnology Inc. (Santa Cruz, Calif.)) or purified from known natural or recombinant sources using conventional methods.

Cdc2 source

The human recombinant enzyme and assay buffer may be obtained commercially (New England Biolabs, Beverly, Mass. USA) or purified from known natural or recombinant sources using conventional methods.

Cdc2 Assay

The protocol used was that provided with the purchased reagents with minor modifications. In brief, the reaction was carried out in a buffer consisting of 50 mM Tris pH 7.5, 100 mM NaCl, 1 mM EGTA, 2 mM DTT, 0.01% Brij, 5% DMSO and 10 mM $MgCl_2$ (commercial buffer) supplemented with fresh 300 µM ATP (31 µCi/ml) and 30 µg/ml histone type IIIss final concentrations. A reaction volume of 80 µL, containing units of enzyme, was run for 20 minutes at 25 degrees C. in the presence or absence of inhibitor. The reaction was terminated by the addition of 120 µL of 10% acetic acid. The substrate was separated from unincorporated label by spotting the mixture on phosphocellulose paper, followed by 3 washes of 5 minutes each with 75 mM phosphoric acid. Counts were measured by a betacounter in the presence of liquid scintillant.

Certain compounds of this invention significantly inhibit cdc2 at concentrations below 50 µM.

PKC kinase source

The catalytic subunit of PKC may be obtained commercially (Calbiochem).

PKC kinase assay

A radioactive kinase assay was employed following a published procedure (Yasuda, I., Kirshimoto, A., Tanaka, S., Tominaga, M., Sakurai, A., Nishizuka, Y. *Biochemical and Biophysical Research Communication* 3:166, 1220–1227 (1990)). Briefly, all reactions were performed in a kinase buffer consisting of 50 mM Tris-HCl pH7.5, 10 mM $MgCl_2$, 2 mM DTT, 1 mM EGTA, 100 µM ATP, 8 µM peptide, 5% DMSO and $^{33}P$ ATP (8 Ci/mM). Compound and enzyme were mixed in the reaction vessel and the reaction initiated by addition of the ATP and substrate mixture. Following termination of the reaction by the addition of 10 µL stop buffer (5 mM ATP in 75 MM phosphoric acid), a portion of the mixture was spotted on phosphocellulose filters. The spotted samples were washed 3 times in 75 mM phosphoric acid at room temperature for 5 to 15 minutes. Incorporation of radiolabel was quantified by liquid scintillation counting.

Erk2 enzyme source

The recombinant murine enzyme and assay buffer may be obtained commercially (New England Biolabs, Beverly, Mass. USA) or purified from known natural or recombinant sources using conventional methods.

Erk2 enzyme assay

In brief, the reaction was carried out in a buffer consisting of 50 mM Tris pH 7.5, 1 mM EGTA, 2 mM DTT, 0.01%

Brij, 5% DMSO and 10 mM $MgCl_2$ (commercial buffer) supplemented with fresh 100 $\mu$M ATP (31 $\mu$Ci/ml) and 30 $\mu$M myelin basic protein under conditions recommended by the supplier. Reaction volumes and method of assaying incorporated radioactivity were as described for the PKC assay (vide supra).

Enzyme Linked Immunosorbent Assay (ELISA) For PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. of Microbiology, Washington, D.C.

The disclosed protocol was adapted for determining activity with respect to a specific PTK. For example, preferred protocols for conducting the ELISA experiment is provided below. Adaptation of these protocols for determining a compound's activity for other members of the receptor PTK family, as well as non-receptor tyrosine kinase, are well within the ability of those in the art. For purposes of determining inhibitor selectivity, a universal PTK substrate (e.g., random copolymer of poly($Glu_4$ Tyr), 20,000–50,000 MW) was employed together with ATP (typically 5 $\mu$M) at concentrations approximately twice the apparent Km in the assay.

The following procedure was used to assay the inhibitory effect of compounds of this invention on KDR, Flt-1, Tie-2, EGFR and ZAP70 tyrosine kinase activity.

Buffers and Solutions:

PGT: Poly (Glu, Tyr) 4:1

Store powder at –20° C. Dissolve powder in phosphate buffered saline (PBS) for 50 mg/ml solution. Store 1 ml aliquots at –20° C. When mixing plates dilute to 250 $\mu$g/ml in Gibco PBS.

Reaction Buffer: 100 mM Hepes, 20 mM $MgCl_2$, 4 mM $MnCl_2$, 5 mM DTT, 0.02% BSA, 200 $\mu$M $MaVO_4$, pH 7.10

ATP: Store aliquots of 100 mM at –20° C. Dilute to 20 $\mu$M in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1 M Phosphoric Acid Procedure 1. Plate Preparation:

Dilute PGT stock (50 mg/ml, frozen) in PBS to a 250 $\mu$g/ml. Add 125 $\mu$l per well of Corning modified flat bottom high affinity ELISA plates (Corning #25805-96). Ad 125 $\mu$l PBS to blank wells. Cover with sealing tape and incubate overnight 37° C. Wash 1× with 250 $\mu$l washing buffer and dry for about 2 hrs in 37° C. dry incubator. Store coated plates in sealed bag at 4° C. until used.

2. Tyrosine Kinase Reaction:

Prepare inhibitor solutions at a 4×concentration in 20% DMSO in water.

Prepare reaction buffer

Prepare enzyme solution so that desired units are in 50 $\mu$l, e.g. for KDR make to 1 mg/$\mu$l for a total of 50 mg per well in the reactions. Store on ice.

Make 4×ATP solution to 20 $\mu$M from 100 mM stock in water. Store on ice Add 50 $\mu$l of the enzyme solution per well (typically 5–50 ng enzyme/well depending on the specific activity of the kinase)

Add 25 $\mu$l 4×inhibitor

Add 25 $\mu$l 4×ATP for inhibitor assay

Incubate for 10 minutes at room temperature

Stop reaction by adding 50 $\mu$l 0.05N HCl per well

Wash plate

**Final Concentrations for Reaction: 5 $\mu$M ATP, 5% DMSO

3, Antibody Binding

Dilute 1 mg/ml aliquot of PY20-HRP (Pierce) antibody (a phosphotyrosine antibody) to 50 ng/ml in 0.1% BSA in PBS by a 2 step dilution (100×, then 200×)

Add 100 $\mu$l Ab per well. Incubate 1 hr at room temp. Incubate 1 hr at 4C.

Wash 4×plate.

4. Color reaction

Prepare TMB substrate and add 100 $\mu$l per well

Monitor OD at 650 nm until 0.6 is reached

Stop with 1M Phosphoric acid. Shake on plate reader.

Read OD immediately at 450 nm.

Optimal incubation times and enzyme reaction conditions vary slightly with enzyme preparations and are determined empirically for each lot. For Lck, the Reaction Buffer utilized was 100 mM MOPSO, pH 6.5, 4 mM $MnCl_2$, 20 mM $MgCl_2$, 5 mM DTT, 0.2% BSA, 200 mM $NaVO_4$ under the analogous assay conditions.

Compounds of formula I can have therapeutic utility in the treatment of diseases involving both identified, including those not mentioned herein, and as yet unidentified protein tyrosine kinases which are inhibited by compounds of formula I. All compounds exemplified herein significantly inhibit KDR kinase at concentrations of 50 micromolar or below. Some compounds of this invention also significantly inhibit other PTKs such as lck at concentrations of 50 micromolar or below.

In Vitro Models for T-cell Activation

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1–7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically $10^5$ responders are mixed with $5 \times 10^4$ stimulators and plated (200 $\mu$l volume) in a U bottom microtiter plate (Costar Scientific). The cells are cultured in RPMI 1640 supplemented with either heat inactivated fetal bovine serum (Hyclone Laboratories), or pooled human AB serum from male donors, $5 \times 10^{-5}$ M 2-mercaptoethanol and 0.5% DMSO, The cultures are pulsed with 0.5 $\mu$Ci of $^3$H thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-vivo Models of T-Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model, BALB/c mice are given 10 μg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ (IFN-γ) and tumor necrosis factor-α(TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57B/6 mice are immunized subcutaneously with 100 μg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at $6\times10^6$ per ml in tissue culture medium (RPMI 1640 supplemented with heat inactivated fetal bovine serum (Hyclone Laboratories), $5\times10^{-5}$ M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560–2566, 1991; murine model: Lab. Invest. 4(3):278, 1981; rodent model:J. Immunol 146 (4):1163–8, 1991). Briefly, mice or rats are immunized with an emulsion of myelin basic protein (MBP), or neurogenic peptide derivatives thereof, and CFA. Acute disease can be induced with the addition of bacterial toxins such as *bordetella pertussis*. Relapsing/remitting disease is induced by adoptive transfer of T-cells from MBP/peptide immunized animals.

CIA may be induced in DBA/1 mice by immunization with type II collagen (J. Immunol:142(7):2237–2243). Mice will develop signs of arthritis as early as ten days following antigen challenge and may be scored for as long as ninety days after immunization. In both the EAE and CIA models, a compound may be administered either prophylactically or at the time of the disease onset. Efficacious drugs should reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

Compounds can also be tested in mouse allograft models, either skin (reviewed in Ann. Rev. Immunol., 10:333–58, 1992; Transplantation:57(12):1701–17D6, 1994) or heart (Am.J.Anat.:113:273, 1963). Briefly, full thickness skin grafts are transplanted from C57BL/6 mice to BALB/c mice. The grafts are examined daily, beginning at day six, for evidence of rejection. In the mouse neonatal heart transplant model, neonatal hearts are ectopically transplanted from C57B/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots.

1. HUVEC cells (from pooled donors) were purchased from Clonetics (San Diego, Calif.) and cultured according to the manufacturer directions. Only early passages (3–8) were used for this assay. Cells were cultured in 100 mm dishes (Falcon for tissue culture; Becton Dickinson; Plymouth, England) using complete EBM media (Clonetics).

2. For evaluating a compound's inhibitory activity, cells were trypsinized and seeded at $0.5–1.0\times10^5$ cells/well in each well of 6-well cluster plates (Costar; Cambridge, Mass.).

3. 3–4 days after seeding, plates were 90–100% confluent. Medium was removed from all the wells, cells were rinsed with 5–10 ml of PBS and incubated 18–24 h with 5 ml of EBM base media with no supplements added (i.e., serum starvation).

4. Serial dilutions of inhibitors were added in 1 ml of EBM media (25 μM, 5 μM, or 1 μM final concentration to cells and incubated for one hour at 37° C. Human recombinant $VEGF_{165}$ (R & D Systems) was then added to all the wells in 2 ml of EBM medium at a final concentration of 50 ng/ml and incubated at 37° C. for 10 minutes. Control cells untreated or treated with VEGF only were used to assess background phosphorylation and phosphorylation induction by VEGF.

All wells were then rinsed with 5–10 ml of cold PBS containing 1 mM Sodium Orthovanadate (Sigma) and cells were lysed and scraped in 200 μl of RIPA buffer (50 mM Tris-HCl) pH7, 150 mM NaCl, 1.% NP-40, 0.25% sodium deoxycholate, 1 mM EDTA) containing protease inhibitors (PMSF 1 mM, aprotinin 1 μg/ml, pepstatin 1 μg/ml, leupeptin 1 μg/ml, Na vanadate 1 mM, Na fluoride 1 mM) and 1 μg/ml of Dnase (all chemicals from Sigma Chemical Company, St. Louis, Mo.). The lysate was spun at 14,000 rpm for 30 min, to eliminate nuclei.

Equal amounts of proteins were then precipitated by addition of cold (−20° C.) Ethanol (2 volumes) for a minimum of 1 hour or a maximum of overnight. Pellets were reconstituted in Laemli sample buffer containing 5% β-mercaptoethanol (BioRad; Hercules, Calif.) and boiled for 5 min. The proteins were resolved by polyacrylamide gel electrophoresis (6%, 1.5 mm Novex, San Diego, Calif.) and transferred onto a nitrocellulose membrane using the Novex system. After blocking with bovine serum albumin (3%), the proteins were probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4° C.

After washing and incubating for 1 hour with HRP-conjugated F(ab)$_2$ of goat anti-rabbit or goat-anti-mouse IgG the bands were visualized using the emission chemiluminescience (ECL) system (Amersham Life Sciences, Arlington Height, Ill.).

Certain examples of the present invention significantly inhibit cellular VEGF-induced KDR tyrosine kinase phosphorylation at concentrations of less than 50 μM.

In Vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829–837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones were purchased from Sigma (St. Louis, Mo.) or Cal Biochem (LaJolla, Calif.) as lyophilized powders and prepared according to supplier instructions.

Vehicle components (DMSO, Cremaphor EL) were purchased from Sigma (St. Louis, Mo.).

Mice (Balb/c, 8–12 weeks old) were purchased from Taconic (Germantown, N.Y.) and housed in a pathogen-free animal facility in accordance with institutional Animal Care and Use Committee Guidelines.

Method:

Day 1: Balb/c mice were given an intraperitoneal (i.p.) injection of 12.5 units of pregnant mare's serum gonadotropin (PMSG).

Day 3: Mice received 15 units of human chorionic gonadotropin (hCG) i.p.

Day 4: Mice were randomized and divided into groups of 5–10. Test compounds were administered by i.p., i.v. or p.o. routes depending on solubility and vehicle at doses ranging from 1–100 mg/kg. Vehicle control group received vehicle only and two groups were left untreated.

Thirty minutes later, experimental, vehicle and 1 of the untreated groups were given an i.p. injection of 17 β-estradiol (500 μg/kg). After 2–3 hours, the animals were sacrificed by CO$_2$ inhalation. Following a midline incision, each uterus was isolated and removed by cutting just below the cervix and at the junctions of the uterus and oviducts. Fat and connective tissue were removed with care not to disturb the integrity of the uterus prior to weighting. Mean weights of treated groups were compared to untreated or vehicle treated groups. Significance was determined by Student's t-test. Non-stimulated control group was used to monitor estradiol response.

Results demonstrate that certain compounds of the present invention inhibit the formation of edema when administered systemically by various routes.

Certain compounds of this invention which are inhibitors of angiogenic receptor tyrosine kinases can also be shown active in a Matrigel implant model of neovascularization. The Matrigel neovascularization model involves the formation of new blood vessels within a clear "marble" of extracellular matrix implanted subcutaneously which is induced by the presence of proangiogenic factor producing tumor cells (for examples see: Passaniti, A., et al, Lab. Investig. (1992), 67(4), 519–528; Anat. Rec. (1997), 249(1), 63–73; Int. J. Cancer (1995), 63 (5), 694–701; Vasc. Biol. (1995), 15(11), 1857–6). The model preferably runs over 3–4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

Certain compounds of this invention which inhibit one or more oncogenic, protooncogenic, or proliferation-dependent protein kinases, or angiogenic receptor PTK also inhibit the growth of primary murine, rat or human xenograft tumors in mice, or inhibit metastasis in murine models.

EXAMPLES

I. Synthesis

The compounds of formula I may be prepared as described below. In the following

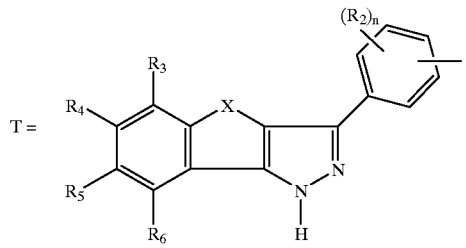

Compounds of formula I in which A represents CONH may be prepared by reacting a compound of formula TL$_1$ COR$_t$ in which R$_t$ is a leaving group for example halo or alkoxy with an amine of formula H$_2$N-L$_2$-R$_1$ at a temperature in the range of 0–250° C. optionally in the presence of a solvent.

Compounds of formula I in which L$_1$A represents CH$_2$NH may be prepared by reacting a compound of formula I in which A represents CONH with a reducing agent, for example lithium aluminium hydride at a temperature in the range of 0–250° C. optionally in the presence of a solvent.

Alternatively, compounds of formula I in which L$_1$A represents CH$_2$NH may be prepared by reacting a compound of formula TL$_1$ CHO with an amine of formula H$_2$N-L$_2$-R$_1$ in the presence of a reducing agent, for example sodium triacetoxyborohydride, at a temperature in the range of 0–250° C. optionally in the presence of a solvent.

Alternatively the group L$_1$-A-L$_2$-R$_1$ may be present in the phenyl ring and the ring system may be constructed as described below in which

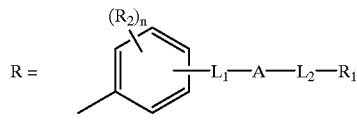

There are two general approaches to the synthesis of the ring systems of the compounds of formula I that have been set in U.S. Pat. No. 3,843,665 and U.S. Pat. No. 3,843,666.

In U.S. Pat. No. 3,843,665, cyclization of the pyrazole ring is effected by heating compounds of formula II with an aromatic sulfonylhydrazide of formula III in an inert solvent and a catalytic amount of an acid. The reaction is carried out for a period of 5 to 30 hours preferably at a temperature of 75° C. to 100° C. and gives compounds of formula I in which $R_1$ is hydrogen.

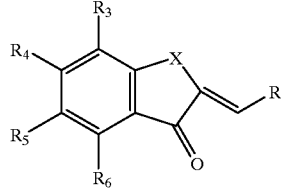

II

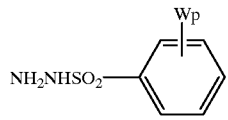

III wherein
  p is 0, 1,2; W is a lower alkyl; and R, $R_3$, $R_4$, $R_5$, $R_6$ and X are as previously defined. Compounds of formula II are prepared by treating an appropriately functionalized compound of formula IV with an aldehyde of formula V in the presence of an acid or base catalyst (Braun, R. A.; Mosher, W. A. J. Amer. Chem. Soc. 1958, 80, 2749).

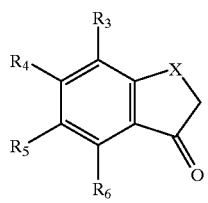

IV

V

A second method of preparing the ring systems of the compound of formula I is set forth in U.S. Pat. No. 3,843,666 where compounds with the general formula VI are heated to 75° C. to 175° C. with a catalytic amount of an organic carboxylic acid or an organic sulfonic acid in an inert solvent such as an aromatic hydrocarbon for a period of 6 to 24 hours.

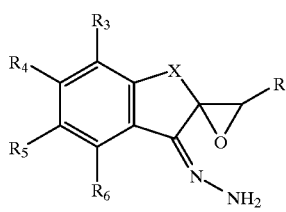

VI wherein: R, $R_3$, $R_4$, $R_5$, $R_6$ and X are as previously defined.
  Compounds of formula VI are prepared by treating compounds of the general formula VII with hydrazine in an inert solvent. The reaction is carried out at 15 to 20° C. for a period of up to 24 hours.

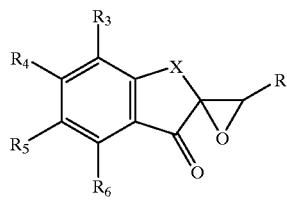

VII

Alternatively compounds of formula I may be prepared directly by reacting a compound of formula VII with hydrazine without isolating the compound of formula VI, for example by heating a compound of formula VII with hydrazine in an inert solvent, e.g. methanol, in the presence of an acid catalyst, e.g. acetic acid, at a temperature in the range from 60° C. to the boiling point of the inert solvent employed.

Compounds of formula I may also be prepared by reacting a compound of formula XVI

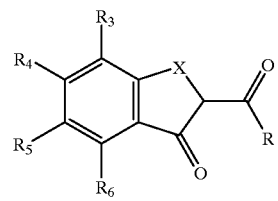

XVI wherein
  R, $R_3$, $R_4$, $R_5$, $R_6$ and X are as previously defined with hydrazine in an inert solvent e.g. methanol, at a temperature in the range of from 15° C. to the boiling point of the inert solvent employed.
  Compounds which have the general formula VII are prepared by treating a compound of formula VIII with an aldehyde of formula V under basic conditions. The reaction is carried out in an inert solvent at a temperature between 5° C. and 10° C. for a period of 3 to 6 hours.

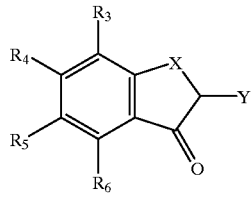

VIII wherein:
  Y is any conventional leaving group, such as chlorine, bromine, iodine, tosylate or mesylate and $R_3$, $R_4$, $R_5$, $R_6$ and X are as previously defined.
  Compounds of formula VII may also be prepared by reacting a compound of formula II with an epoxidizing agent, for example hydrogen peroxide, in an inert solvent, for example methanol, dichloromethane, water or mixtures thereof, at a temperature in the range of 0° to 100° C. optionally in the presence of a base, for example sodium hydroxide.

Cyclization of VI can also be effected by treatment with a mineral acid such as hydrochloric acid, sulfuric acid or phosphoric acid. The reaction is carried out in a lower alkanol at a temperature between 15° C. to 20° C. for a period of 12 to 48 hours. The product of the reaction, IX, can then be aromatized to I by heating to a temperature of 50° C. to 150° C. with an organic carboxylic acid or an organic sulfonic acid in a straight chain ether or cyclic ether for the period of 8 to 30 hours.

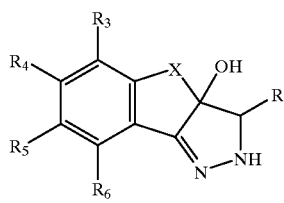

IX

Compound IX can be diacetylated by treatment with an acid anhydride of formula $(R_xCO)_2O$ (structure X) in which $R_x$ is a $C_{1-6}$ alkyl group in an inert solvent such as an aromatic hydrocarbon at a temperature between 35° C. to 200° C. for a period of 5 to 8 hours to give a compound of formula XI

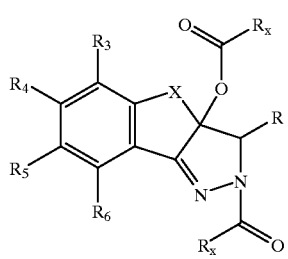

XI

Compound XI can then be aromatized to compound XII by heating to a temperature of 35° C. to 200° C. with a mineral acid or an organic acid in an inert solvent for the period of 4 to 8 hours. Finally, compound XII can be converted to I by heating to a temperature of 50° C. to 150° C. in an inert solvent such as water or a lower alcohol in the presence of an alkali metal or an alkali metal hydroxide for the period of 8 to 30 hours.

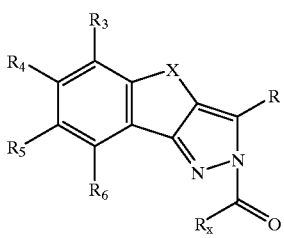

XII

Compounds with the general formula II can be cyclized to compounds of formula XIII by reaction with hydrazine in an inert solvent, for example methanol, at a temperature in the range of 35–150° C.

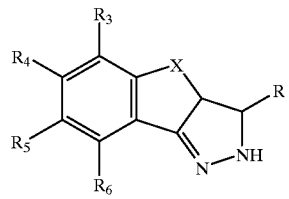

XIII

Compounds of formula I may be prepared by reacting a compound of formula XIII with a dehydrogenating agent, for example sulphur, oxygen, palladium, manganese dioxide or lead dioxide optionally in the presence of an inert solvent, for example a hydrocarbon, at a temperature in the range of 15 to 250° C.

Specific examples of the above transformations can be found in U.S. Pat. Nos. 3,843,665 and 3,843,666.

The bridging carbonyl can be transformed to a methylene group via a Wolf-Kishner reduction of the corresponding hydrazone (Mosher, W. A., Tawfik, E.-Z., Lipp, D. W. J. Org. Chem. 1971, 36, 3890).

Additional methods for functionalization of the bridging carbonyl and specific examples can be found in Japanese Patent Application JP 60 130521 A2, and B. Loev, U.S. Pat. No. 3,004,983 (1960).

Compounds of formula I may be prepared by reacting a compound of formula XIV

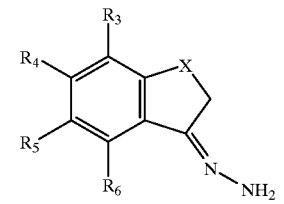

XIV with a strong base, for example n-butyllithium at a temperature in the range of −78° C. to 25° C., followed by reaction with a compound of formula $R_2COG$ (structure XV) in which $R_2$ is as previously defined and G represents a $C_{1-6}$ alkoxy group.

Compounds of formula IV, VIII, XIV, XV and XVI are commercially available or may be prepared by methods known to those skilled in the art.

Compounds of formula I in which X represents SO, or $SO_2$ may be prepared by oxidizing a compound of formula I in which X represents S by methods known to those skilled in the art for example by using an appropriate number of molar equivalents of 3-chloroperbenzoic acid.

Compounds of formula I in which X represents a group of formula —C=$NOR_7$ may be prepared by reacting a compound of formula I in which X represents carbonyl, with a compound of formula $H_2NOR_7$ by methods known to those skilled in the art.

Compounds represented by formula Ia in which X is a methylene group that is optionally substituted with a $C_{1-6}$ alkyl group can be prepared from a 1-indanone (XVII) and a phenyl 4-halobenzoate (XVIII) as shown in Scheme I.

Scheme I:
Synthesis of compounds represented by formula Ia in which X is an optionally substituted methylene.

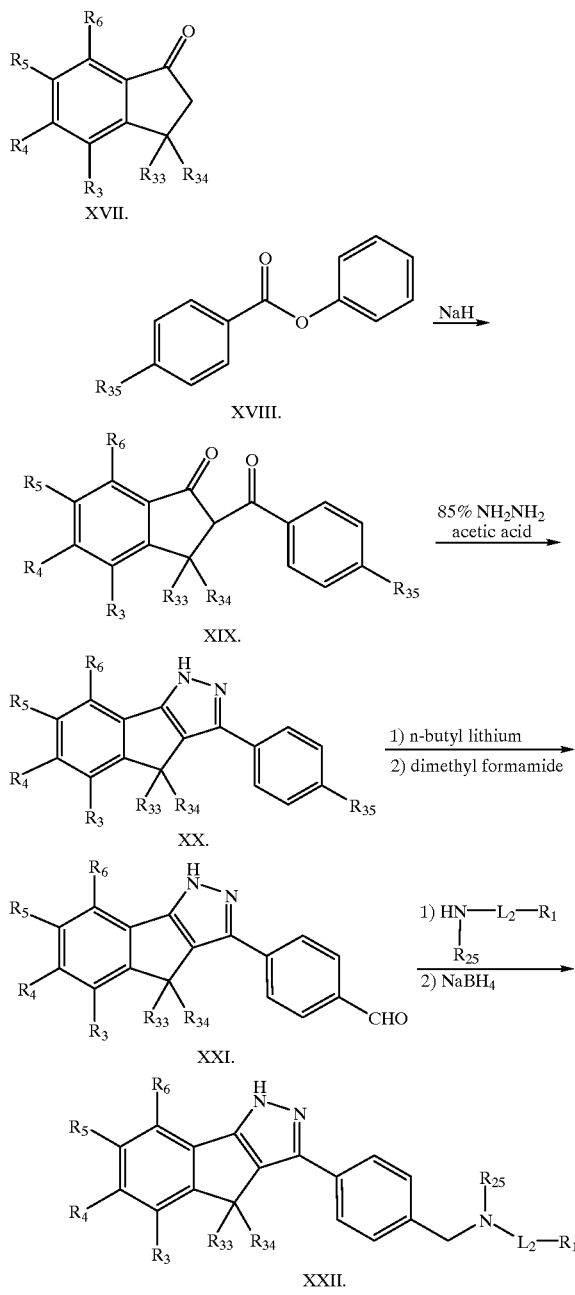

$R_{35}$ = a halide
$R_{33}$ and $R_{34}$ are each, independently, H or $C_{1-6}$ A compound of formula Ia wherein X is a carbonyl can be prepared from a compound represented by formula XXI in which the bridgehead methylene group is unsubstituted (see Scheme II). The aldehyde of the compound represented by formula XXI is converted into an ester, then the pyrazole ring is protected with an amine protecting group (Pro= protecting group in Scheme II), such as 4,4'-dimethoxydiphenylmethyl. The compound thus formed (compound XXIII) is treated with chromium trioxide to form a carbonyl group at the bridgehead carbon. This compound is treated with diisobutylaluminum hydride (DIBAL-H) which converts the carbonyl and the ester to a hydroxy group. A Swern oxidation reforms the bridgehead carbonyl and converts the other hydroxy group to an aldehyde. The aldehyde can be converted to an aminomethyl group by the method shown in Scheme I, or it can be selectively reduced with hydrogen gas and platinum(IV) oxide catalyst to a hydroxy group. The hydroxy group is treated with tosyl or mesyl chloride to form a good leaving group and is substituted with an amine.

Alternatively, the carbonyl bridgehead can be prepared from a compound represented by formula XXI in which the methylene bridgehead is unsubstituted by the method of Scheme III. In this method, the pyrazole ring is protected with an amine group, and the aldehyde is protected as an acetal. The compound thus formed (compound XXIX) is treated with chromium trioxide in pyridine to form the carbonyl bridgehead. The acetal protecting group can then be removed to reform the aldehyde which can be converted to an aminomethyl group by the methods depicted in Schemes I or II.

Scheme II:
Method of synthesizing compounds having a carbonyl bridgehead.

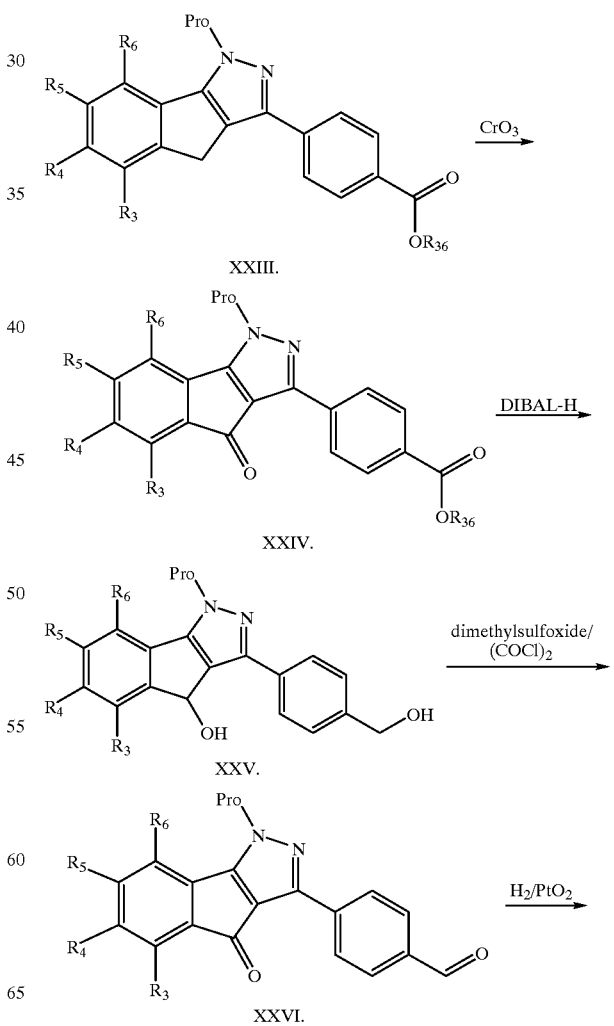

-continued

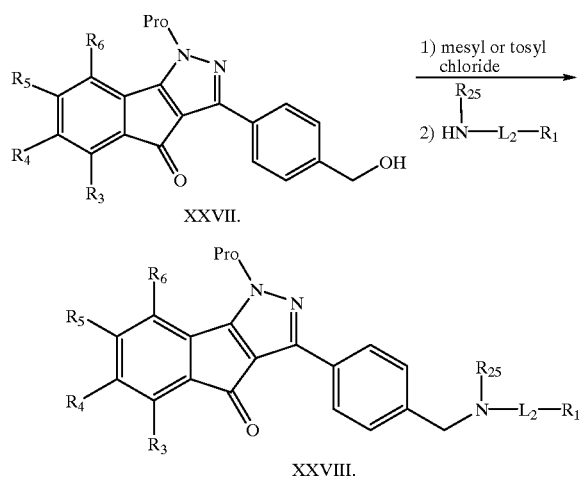

Scheme III:
Method of synthesizing compounds having a carbonyl bridgehead.

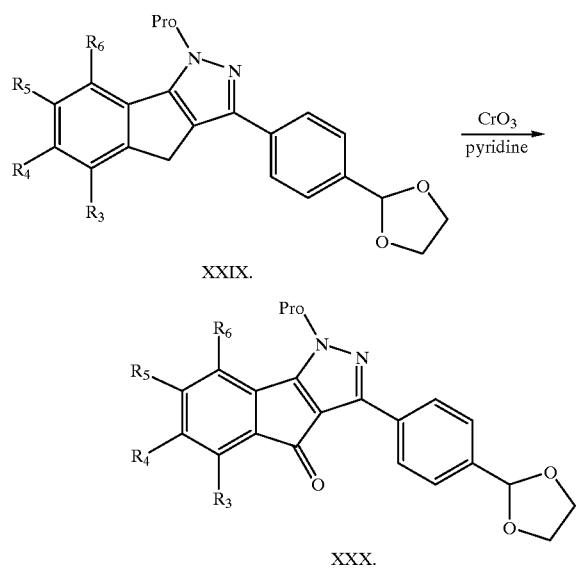

Compounds represented by formula Ia in which X is $SO_2$ can be prepared from a 4-(1H-benzo[4,5]thieno[3,2-c]pyrazol-3-yl)-toluene by the method depicted in Scheme IV. A 4-(1H-benzo[4,5]thieno[3,2-c]pyrazol-3-yl)-benzaldehyde can be synthesized as depicted in Scheme V and can be reduced to form a 4-(1H-benzo[4,5]thieno[3,2-c]pyrazol-3-yl)-toluene with, for example, $NaBH_4$.

Scheme IV:
Method of synthesizing compounds having $SO_2$ bridgehead.

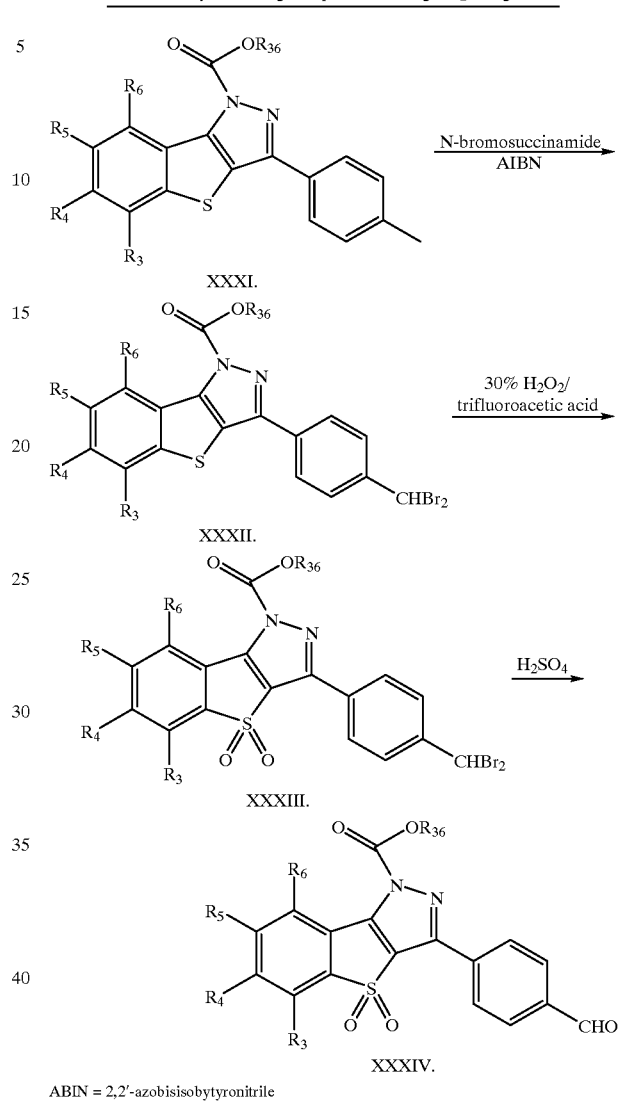

ABIN = 2,2'-azobisisobytyronitrile

Scheme V:
Method of synthesizing a 4-(1H-benzo[4,5]thieno[3,2-c]pyrazol-3-yl)-benzaldehyde.

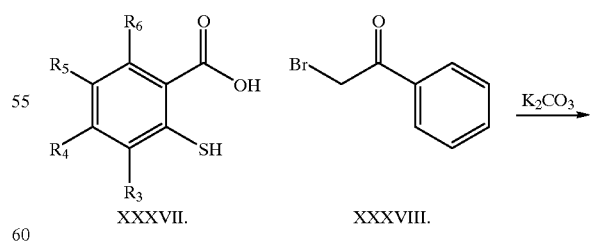

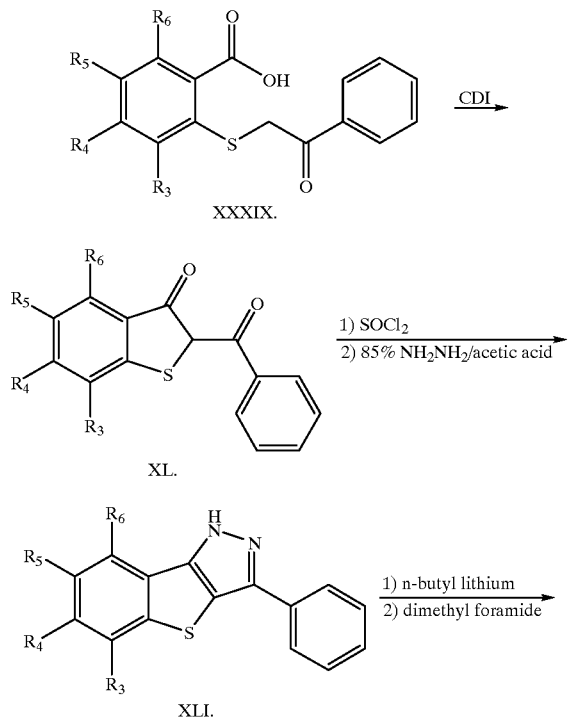

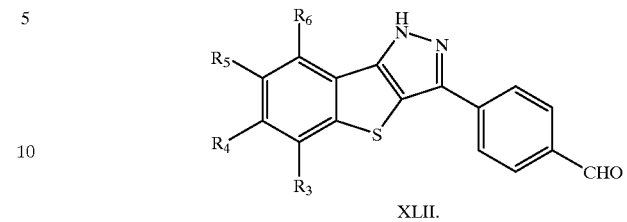

The key intermediate represented by formula XXI can also be synthesized by treating a 3-iodo-1,4-dihydro-indeno[1,2-c]pyrazole with phenyl borane coupling agent in the presence of palladium triphenylphosphine catalyst (see Scheme VI and Tables I and II). In the reactions carried out in Table I, the starting material was 3-iodo-1,4-dihydro-indeno[1,2-c]pyrazole. In the reactions carried out in Table II, the starting material was 3-iodo-1,4-dihydro-indeno[1,2-c]pyrazole in which the pyrazole ring was protected with 4,4'-dimethoxydiphenylmethyl.

Scheme VI:
Method of preparing a 4-(1,4-dihydro-indeno[1,2-c]pyrazol-3-yl)benzaldehyde.

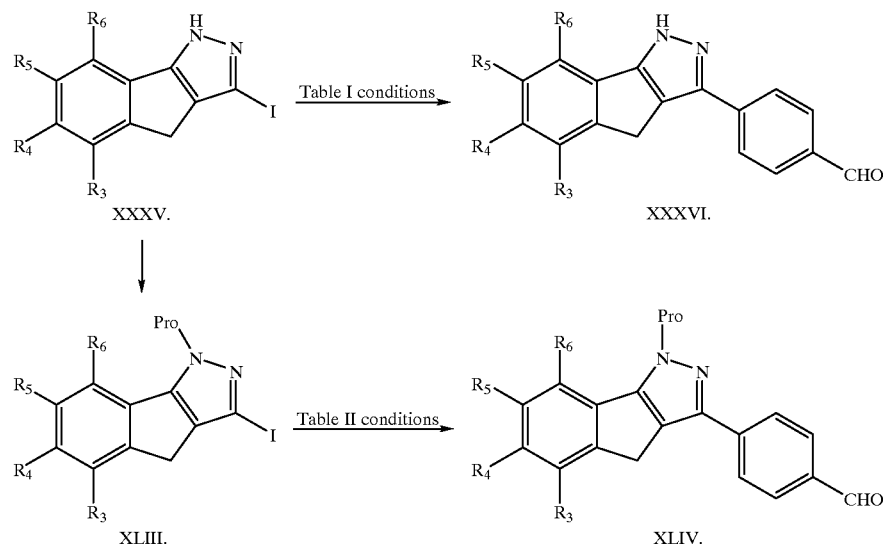

TABLE I

| Entry | Coupling Agent | Base | Pd catalyst | Conditions | Yield of XXXVI |
|---|---|---|---|---|---|
| 1 | 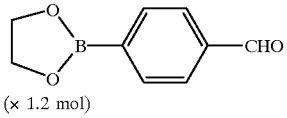 (× 1.2 mol) | $K_3PO_4$ (× 1.5 mol) | $Pd(PPh_3)_4$ (× 5 mol %) | 100 deg, 20 h in DMF (under $N_2$) | 43% (isolated) |
| 2 | 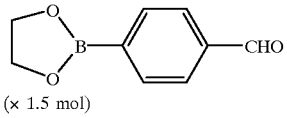 (× 1.5 mol) | $K_3PO_4$ (× 1.5 mol) | $Pd(PPh_3)_4$ (× 5 mol %) | 100 deg, 24 h in DMF (under $N_2$) | 39% (isolated) |
| 3 | 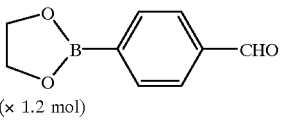 (× 1.2 mol) | $K_3PO_4$ (× 1.5 mol) | $PdCl_2(PPh_3)_2$ (× 5 mol %) | 100 deg in DMF (under $N_2$) | Small amount (by TLC) |
| 4 | 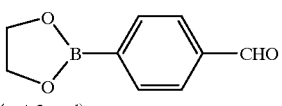 (× 1.2 mol) | $K_3PO_4$ (× 1.5 mol) | $Pd(PPh_3)_4$ (× 5 mol %) | 100 deg in NMP (under $N_2$) | Small amount (by TLC) |

In general, protection of the pyrazole ring of XXXV before addition of the coupling agent improves the product yield.

TABLE II

| Entry | Coupling Agent | Base | Pd catalyst | Conditions | Yield of XLIV |
|---|---|---|---|---|---|
| 1 | 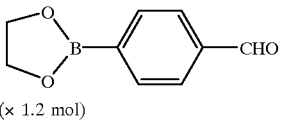 (× 1.2 mol) | $K_3PO_4$ (× 1.5 mol) | $Pd(PPh_3)_4$ (× 5 mol %) | 100 deg, 15 h in DMF (under $N_2$) | 81% (isolated) |
| 2 | 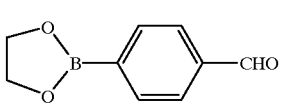 (× 1.5 mol) | $K_3PO_4$ (× 1.5 mol) | $Pd(PPh_3)_4$ (× 5 mol %) | 100 deg, 24 h in DMF (under $N_2$) | 79% (isolated) |
| 3 | 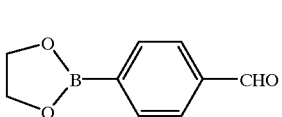 (× 1.2 mol) | $K_3PO_4$ (× 1.5 mol) | $PdCl_2(PPh_3)_2$ (× 5 mol %) | 100 deg, 29 h in DMF (under $N_2$) | 80% (isolated) |
| 4 | 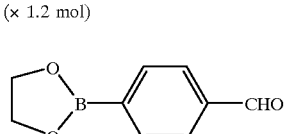 (× 1.2 mol) | $K_3PO_4$ (× 1.5 mol) | $Pd(PPh_3)_4$ (× 5 mol %) | 100 deg, 32 h in NMP (under $N_2$) | 50% (isolated) |
| 5 | 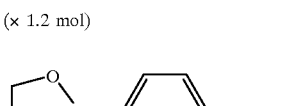 (× 1.2 mol) | $K_3PO_4$ (× 1.5 mol) | $Pd(PPh_3)_4$ (× 5 mol %) | 100 deg, 24 h in 1,4-dioxane (under $N_2$) | Small amount (by TLC) |

TABLE II-continued

| Entry | Coupling Agent | Base | Pd catalyst | Conditions | Yield of XLIV |
|---|---|---|---|---|---|
| 6 | (structure) (× 1.2 mol) | $K_3PO_4$ (× 1.5 mol) | $Pd(PPh_3)_4$ (× 5 mol %) | 100 deg, 2 h in 2-methoxy-ethanol (under $N_2$) | 80% (isolated) |
| 7 | (structure) (× 1.2 mol) | $K_2CO_3$ (× 1.1 mol) | $Pd(PPh_3)_4$ (× 5 mol %) | 100 deg, 6 h in DMF (under $N_2$) | 77% (isolated) |
| 8 | (structure) (× 1.2 mol) | $K_3PO_4$ (× 1.5 mol) | $Pd(PPh_3)_4$ (× 5 mol %) | 100 deg, 24 h in DMF (under $N_2$) | Small amount (by TLC) |

Compound XXXV can be prepared by treating a 1-indanone (XLV) with sodium hydride then adding a formate ester, such as ethyl formate to form compound XLVI. Compound XLVI is then treated with hydrazine and acetic acid in ethanol to form a 1,4-dihydro-indeno[1,2-c]pyrazole (XLVII). The 1,4-dihydro-indeno[1,2-c]pyrazole is treated with N-iodosuccinimide in dimethyl formamide to form Compound XXXV (see Scheme VII).

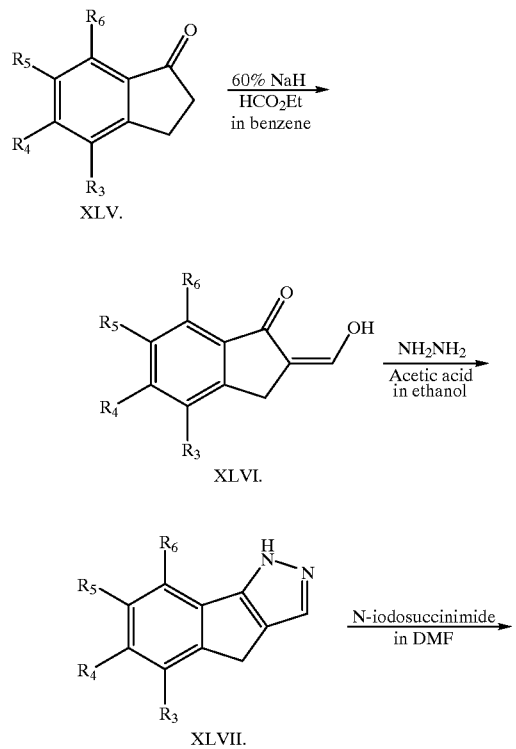

Scheme VII:
Synthesis of Compound XXXV.

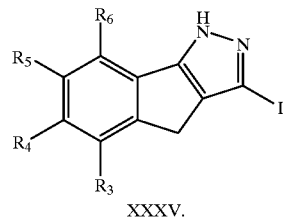

XXXV.

Compounds of formula I in which $R_1$=4-pyridyl may be further functionalized in the 2-position of the pyridine ring by methods known to those skilled in the art, for example, via pyridine-N-oxide mediated rearrangements.

Certain substituents in compounds of formula I may be interconverted by methods known to those skilled in the art. For example alkoxy substituents may be reacted with a suitable ether cleaving reagent for example hydrobromic acid, boron tribromide or pyridine hydrochloride to give a compound of formula I with a hydroxy substituent. Alternatively compounds of formula I with an alkoxy substituent may be prepared by alkylating compounds of formula I which have a hydroxy substituent. Carboxylic ester substituents may be converted into carboxy or amide substituents and carboxylic acid substituents may be converted into carboxylic ester or amide substituents. Nitro substituents may be reduced to amines and amines may be acylated by methods known to those skilled in the art.

It will be appreciated by those skilled in the art that certain substituents may react with some of the reagents described in the above processes. In such cases an alternative process should be used or the reactive substituent should be protected prior to the reaction and deprotected after the reaction.

The invention is illustrated by the following Examples which are given by way of example only. The final product of each of these Examples was characterized by one or more of the following procedures: high performance liquid chromatography; elemental analysis, nuclear magnetic resonance spectroscopy, infrared spectroscopy and high resolution mass spectroscopy. The following abbreviations are used IMS=industrial methylated spirit
LCMS=liquid chromatography/mass spectroscopy.

EXAMPLE 1 a) A mixture of indan-1-one (3.3 g), methyl 4-formylbenzoate (5.0 g), piperidine (0.6 ml) and glacial acetic acid (0.5 ml) was heated on a steam bath for 3 hours. The solid mass obtained was boiled up in industrial methylated spirits (200 ml) and then hot filtered. The solid residue obtained was washed with industrial methylated spirits and dried to give methyl 4-(1-oxoindan-2-ylidenemethyl)benzoate, m.p. 194–198° C.

b) The product from a) (1.5 g) was suspended in methanol (10 ml) and dichloromethane (15 ml) and stirred at 0–5° C. whilst 2M sodium hydroxide solution (2.7 ml) was added followed by 30% hydrogen peroxide (100 vol. 1.1 ml). The mixture was stirred at 0–5° C. for 5 minutes then at ambient temperature for 24 hours. Dichloromethane (100 ml) was added to the mixture which was then washed with brine (2×50 ml), dried, filtered and evaporated to give methyl 4-(1-oxospiro[indan-2,2'-oxiran]-3'-yl)benzoate, m.p. 160–163° C. The aqueous phase was acidified with 5M hydrochloric acid and extracted with dichloromethane to give 4-(1-oxospiro[indan-2,2'-oxiran]-3'-yl)benzoic acid, m.p. 220° C. with decomposition c) 4-(1-Oxospiro[indan-2,2'-oxiran]-3'-yl)benzoic acid from part b) (780 mg), methanol (50 ml), hydrazine hydrate (0.18 ml) and glacial acetic acid (6 drops) were boiled under reflux for 24 hours. The mixture was cooled in ice and filtered to give 4-(1,4-dihydroindeno[1,2-c]pyrazol-3-yl)benzoic acid, m.p. >320° C.

d) A mixture of the product from c) (5.3 g) and dichloromethane (250 ml) was stirred at ambient temperature and then oxalyl chloride (5 ml) and dry N,N-dimethylformamide (6 drops) were added, the mixture was stirred at ambient temperature for 10 minutes and then boiled under reflux for 90 minutes. The solvent was removed under reduced pressure to give a crude acid chloride which was used directly in the next experiment.

e) The acid chloride from d) (3.73 g) was stirred at ambient temperature in dichloromethane (150 ml), then triethylamine (3 ml) and then 4-aminopyridine (0.9 g) were added. The mixture was stirred at ambient temperature for 3 hours. Water (150 ml) and 5M sodium hydroxide solution (50 ml) were added and the mixture was stirred for 90 minutes at ambient temperature. The mixture was filtered and the residue was washed with dichloromethane and water. The filtrate and washings were combined, separated and the dichloromethane layer was dried and evaporated to give a solid which was combined with the original solid obtained from the filtration and separated by flash column chromatography on silica using dichloromethane/ethyl alcohol (10:1) to give N-(4-pyridyl)-4-(1,4-dihydroindeno[1,2-c]pyrazol-3-yl)-benzamide.

f) Lithium aluminium hydride (830 mg) was added in portions to a stirred mixture of the product from e) (1.9 g) in dry tetrahydrofuran (50 ml) at ambient temperature. The mixture was boiled under reflux for 1 hour. The mixture was cooled to 0–5° C. and added to ethyl acetate (70 ml) and then water (70 ml) was added. The mixture was stirred for 10 minutes and filtered to give a solid A. The aqueous layer was separated off and extracted with further ethyl acetate (100 ml). The solid A was stirred with ethanol and filtered. The ethyl acetate extracts and the ethanol filtrate were combined and evaporated. The residue obtained was purified by flash column chromatography using dichloromethane/ethanol (10:1) to give 4-(1,4-dihydroindeno[1,2-c]pyrazole)-N-(4-pyridyl)benzylamine, m.p. 270–274° C.

EXAMPLE 2 a) A mixture of indan-1-one (20.0 g), 4-nitrobenzaldehyde (27.0 g), glacial acetic acid (3.0 g) and piperidine (3.06 g) was heated at 95° C. under nitrogen for 3.5 h. The mixture was cooled to 20° C. and filtered to give a solid which was recrystallized from industrial methylated spirit to give 2-(4-nitrobenzylidene)indan-1-one.

b) The product from a) (28.0 g) was stirred with dichloromethane (100 ml) and methanol (100 ml) at 20° C. and then 2M sodium hydroxide solution (50 ml) was added followed by hydrogen peroxide (20 ml, 100 volumes). The mixture was stirred at 20° C. for 24 hours. Further hydrogen peroxide (10.0 ml, 100 volumes) was added and the mixture was stirred for a further 24 hours. Further hydrogen peroxide (10 ml, 100 volumes) was added and the mixture was stirred for 64 hours. The reaction mixture was neutralized with glacial acetic acid and the solid which formed was collected by filtration and dried to give 3'-(4-nitrophenyl)-1-oxospiro[indan-2,2'-oxirane].

c) The product from b) (10.0 g) was dissolved in ethanol (180 ml) and hydrazine hydrate (1.78 g) was added to the solution obtained, followed by glacial acetic acid (30 drops). The mixture was boiled under reflux for 5 hours and then cooled to 20° C. and stood at this temperature for 18 hours. The solid was collected by filtration and recrystallized from acetone to give 3-(4-nitrophenyl)-1,4-dihydroindeno[1,2-c]pyrazole, m.p. 267–270° C.

d) The product from c) (3.0 g) was suspended in industrial methylated spirit (200 ml) and 5% palladium on charcoal (250 mg) was added followed by ammonium formate (2.05 g). The mixture was stirred and heated at 70° C. for 3 hours and then cooled to ambient temperature and then filtered. The filtrate was concentrated under reduced pressure and triturated with dichloromethane to give 4-(1,4-dihydroindeno[1,2-c]pyrazol-3-yl)aniline, m.p. 253–254° C.

e) The product from d) (1.0 g) was dissolved in dichloromethane (30 ml) and triethyamine (0.62 ml) was added. The mixture was cooled to 0° C. and benzene sulphonyl chloride (0.79 g) was added with stirring. The mixture was warmed to 20° C. and stirred at this temperature for 2 hours. Further triethylamine (0.62 ml) and benzene sulphonyl chloride (0.79 g) were added and the mixture was stirred at ambient temperature for 4 hours and then allowed to stand at ambient temperature for 16 hours. Ether (80 ml) was added, followed by water (40 ml). The solid which precipitated was collected by filtration, washed with sodium bicarbonate solution and ether and then dried under vacuum at 60° C. The material was recrystallized from acetone to give a solid which was purified by flash column chromatography on silica using dichloromethane to give a solid which was identified as 4'-(1-phenylsulphonyl(1,4-dihydroindeno[1,2-c]pyrazol-3-yl) N-phenylsulphonylaniline.

f) The product from e) (0.56 g) was suspended in methanol (40 ml) and 2M sodium hydroxide solution (5.3 ml) was added. A clear solution was obtained and this was stirred at 20° C. for 20 minutes. The mixture was poured into 2M hydrochloric acid (75 ml) and the solid obtained was collected by filtration to give a solid which was stirred with saturated sodium bicarbonate (25 ml) and ethyl acetate (25 ml) for 30 minutes and then filtered to give N-[4-(1,4-dihydroindeno[1,2-c]pyrazol-3-yl)phenyl]benzenesulphonamide, m.p. 286–288° C.

EXAMPLE 3

A mixture of the acid chloride from Example 1 d) (100 mg) dichloromethane (5 ml), 2-methoxyethanol (26 μl) and triethylamine (84 μl) was stirred at ambient temperature for 20 hours. The mixture was stirred with sodium bicarbonate solution (5 ml saturated) and filtered. The filtrate was evaporated to give a solid which was purified by flash column chromatography using dichloromethane/industrial methylated spirits (25:2) as the mobile phase to give 4-(1,4-dihydroindeno[1,2-c]pyrazol-3-yl)-N-(2-methoxyethyl) benzamide as a colourless solid.

EXAMPLE 4

A mixture of the acid chloride from Example 1 d) (100 mg), dichloromethane (5 ml), 4-nitroaniline (41 mg) and triethylamine (64 μl) was stirred at ambient temperature for 20 hours. The mixture was stirred with saturated sodium bicarbonate solution (5 ml) for 10 minutes and then filtered. The solid was washed with dichloromethane, then with alcohol and dried to give 4-(1,4-dihydroindeno[1,2-c]pyrazol-3-yl)-N-(4-nitrophenyl)benzamide as a colourless solid.

EXAMPLE 5 a) The aniline from Example 2 d) (6 g) was dissolved in dichloromethane (200 ml) and then triethylamine (7.4 ml) was added. The mixture was cooled to 0° C. and then chloroacetyl chloride (4.2 ml) was added with stirring and the mixture was warmed to 20° C. The mixture was filtered and the solid obtained was washed with water and then ether and dried to give an intermediate which had been chloroacetylated on the 1-nitrogen of the pyrazole and on the NH$_2$ group of the starting aniline.

b) The product from a) (1.4 g), imidazole (0.95 g) and tetrahydrofuran (40 ml) were boiled under reflux at 90° C. under nitrogen for 6 hours. The mixture was filtered and the filtrate was evaporated under reduced pressure to give a residue which was partitioned between ethyl acetate and 2M hydrochloric acid. The solid obtained was collected by filtration and dried to give 4-(1,4-dihydroindeno[1,2-c]pyrazol-3-yl)imidazol-1-ylacetanilide dihydrochloride, m.p. 264–266° C.

EXAMPLE 6

The product from Example 5 (0.27 g) was suspended in tetrahydrofuran (30 ml) under nitrogen with stirring and lithium aluminium hydride (87 mg) was added. The mixture was stirred at 20° C. for 18 hours. The mixture was quenched with a saturated solution of sodium sulphate (40 ml) and then extracted with ethyl acetate (2×30 ml) to give a solid which was dissolved in ethanol (3 ml) to which concentrated hydrochloric acid (10 drops) was added. The ethanol was removed to give a yellow solid which was triturated with ether to give 4-(1,4-dihydroindeno[1,2-c]pyrazol-3-yl)-N-[2-(imidazol-1-yl)ethyl]aniline dihydrochloride, m.p. 205–209° C.

EXAMPLE 7 a) A mixture of 4-cyanobenzene sulphonyl chloride (5.15 g) in acetone (70 ml) was stirred at ambient temperature and then a solution of 2-morpholinoethylamine (6.7 ml) in acetone (15 ml) was added dropwise with stirring. The mixture was stirred at ambient temperature for 2 hours and then the acetone was removed by evaporation and the residue was eluted through a silica pad using ethyl acetate to give 4-cyano-N-2-morpholinoethyl-benzenesulphonamide.

b) The product from a) (0.65 g) and dry toluene (30 ml) were stirred at 0–5° C. and diisobutylaluminum hydride (4.4 ml of a 1.0M solution in cyclohexane) was added at 0–5° C. After the addition the solution was warmed to ambient temperature over 30 minutes and then warmed to boiling under reflux over 30 minutes and boiled for 3 hours. The mixture was cooled and added to 5M hydrochloric acid (10 ml) at 10–15° C. The mixture was then warmed to 90° C. for 10 minutes and then cooled and the toluene layer was separated off. The aqueous layer was washed with ethyl acetate and then neutralized to pH 7–8 using 5M sodium hydroxide solution. This mixture was extracted with ethyl acetate, dried, filtered and evaporated to give a gum which was dried under vacuum at 40° C. to give a solid which was identified as 4-formyl-N-(2-morpholinoethyl)benzene sulphonamide, m.p. 114–116° C.

c) The product from b) (200 mg), 2-bromoindanone (142 mg) and dry methanol (3 ml) were stirred at 0° C., and to this mixture was added a solution of sodium methoxide (44 mg) in methanol (0.5 ml). The mixture was stirred at 0° C. for 2 hours to give a solid which was collected by filtration, washed with methanol and dried under vacuum to give the epoxide.

d) The product from c) (3.7 g) hydrazine hydrate (1 ml), glacial acetic acid (10 drops) and ethanol (100 ml) were boiled under reflux for 26 hours and the ethanol dried over molecular sieves in a Soxhlet extractor. The solvent was removed under reduced pressure and the residue was purified by flash column chromatography to give 4-(1,4-dihydroindeno[1,2-c]pyrazol-3-yl)-N-(2-morpholinoethyl)benzenesulphonamide, m.p. 218–220° C.

EXAMPLE 8

This was prepared in a similar manner to Example 7 except that 2-methoxyethylamine was used instead of 2-morphoninoethylamine and the product obtained was 4-(1,4-dihydroindeno[1,2-c]pyrazol-3-yl)-N-(2-methoxyethyl) benzenesulphonamide.

EXAMPLE 9 a) A mixture of indan-1-one (3.3 g), methyl 4-formylbenzoate (5.0 g), piperidine (0.6 ml) and glacial acetic acid (0.5 ml) was heated on a steam bath for 3 hours. The solid mass obtained was boiled up in industrial methylated spirits (200 ml) and then hot filtered. The solid residue obtained was washed with industrial methylated spirits and dried to give methyl 4-(1-oxoindan-2-ylidenemethyl)benzoate, m.p. 194–198° C.

b) The product from a) (1.5 g) was suspended in methanol (10 ml) and dichloromethane (15 ml) and stirred at 0–5° C. whilst 2M sodium hydroxide solution (2.7 ml) was added followed by 30% hydrogen peroxide (100 vol. 1.1 ml). The mixture was stirred at 0–5° C. for 5 minutes then at ambient temperature for 24 hours. Dichloromethane (100 ml) was added to the mixture which was then washed with brine (2×50 ml), dried, filtered and evaporated to give methyl 4-(1-oxospiro [indan-2,2'-oxiran]-3'-yl)benzoate, m.p. 160–163° C. The aqueous phase was acidified with 5M hydrochloric acid and extracted with dichloromethane to give 4-(1-oxospiro[indan-2,2'-oxiran]-3'-yl)benzoic acid, m.p. 220° C. with decomposition.

c) A mixture of methyl 4-(1-oxospiro[indan-2,2'-oxiran]-3'-yl)benzoate (750 mg), methanol (30 ml) and hydrazine hydrate (0.16 ml) was stirred at ambient temperature whilst glacial acetic acid (6 drops) was added. The mixture was boiled under reflux for 24 hours and then allowed to stand at ambient temperature for 24 hours, then cooled to 0° C. and filtered to give methyl (4-(1, 4-dihydroindeno[1,2-c]pyrazol-3-yl)benzoate, m.p. 224–226° C.

d) The ester from c) (2.20 g) and N,N-diethylethylenediamine (7 ml) were boiled under reflux for 4.5 hours. The mixture was cooled to ambient temperature and then petroleum ether, b.p. 40–60° C. (50 ml) was added. The mixture was filtered to give the amide.

e) The amide (2.75 g) was suspended in tetrahydrofuran (80 ml) and stirred at ambient temperature under nitrogen as lithium aluminium hydride (1.14 g) was added. The mixture was stirred for 3.5 hours and then further lithium aluminium hydride (1.14 g) and tetrahydrofuran (40 ml) were added. A third portion of lithium aluminium hydride was added after 22.5 hours and this mixture was then stirred for 24 hours. The mixture was boiled under reflux for 2.5 hours then stood overnight at ambient temperature. The mixture was stirred under nitrogen with cooling in an ice-bath while ethyl acetate (100 ml) was added, followed by water (100 ml) the organic layer was separated off, washed, dried and evaporated to give an oil which was purified by flash column chromatography on silica using ethyl acetate/ethanol/triethylamine (7:2:1). Appropriate fractions were combined and evaporated to give a gum (0.85 g) which was dissolved in ethanol (5 ml) with warming and to the solution was added concentrated hydrochloric acid (0.6 ml). The mixture was then evaporated under reduced pressure and the residual gummy solid was boiled with ethanol (10 ml) then cooled in ice and filtered to give N-[2-(N,N-diethylamino)ethyl]-4-(1,4-dihydroindeno[1,2-c]pyrazol-3-yl)benzylamine trihydrochloride, m.p. 225° C.

EXAMPLE 10

This example was prepared in a similar manner to Example 7 except that N,N-diethylaminoethylamine was used instead of 2-morpholinoethyl amine. The product obtained was N-[2-(N,N-diethylamino)ethyl]-4-(1,4-dihydroindeno[1,2-c]pyrazol-3-yl)benzenesulphonamide dihydrochloride, m.p. 192–196° C.

EXAMPLE 11

This example was prepared in a similar manner to Example 9 using 2-morpholinoethylamine instead of N,N-diethylethylenediamine. The product obtained was 4-(1,4-dihydroindeno[1,2-c]pyrazol-3-yl)-N-(2-morpholinoethyl) benzylamine dihydrochloride, m.p. 266–269° C. (with decomposition).

EXAMPLE 12

This was prepared in a similar manner to Example 1 except that 4-ethoxyaniline was used instead of 2-methoxyethylamine. The product obtained was N-(4-ethoxyphenyl)-4-(1,4-dihydroindeno[1,2-c]pyrazol-3-yl) benzylamine, m.p. 180° C. (with decomposition).

EXAMPLE 13

This was prepared in a similar manner to Example 9 d) except that (S-(+)-2-(aminomethyl)pyrrolidine was used instead of N,N-diethylethylenediamine. The product obtained was (S)-4-(1,4-dihydroindeno[1,2-c]pyrazol-3-yl)-N-(pyrrolidin-2-ylmethyl)benzamide dihydrochloride, m.p. 222–226° C.

EXAMPLE 14 a) Methyl thiosalicylate (9.89 ml) was added to a solution of sodium methoxide (11.6 g) in ethanol (100 ml) with stirring. After 15 minutes a solution of 4'-bromophenacyl bromide (20.0 g) in ethanol (100 ml) was added and the mixture was stirred and boiled under reflux for 18 hours. The mixture was cooled and acidified with 10% hydrochloric acid (150 ml). The solid was collected and used directly in the next experiment.

b) The product from a) (18.0 g) was stirred and boiled under reflux in ethanol (150 ml) in a flask fitted with a Soxhlet extractor thimble containing 4 Å molecular sieves. 1 Drop of glacial acetic acid was added followed by hydrazine hydrate (3.9 ml) and the mixture was boiled and stirred under reflux for 64 hours. The mixture was cooled and the precipitate was collected and used directly in the next experiment.

c) The product from b) (4.0 g) was dissolved in tetrahydrofuran (200 ml) and added dropwise with stirring at 0° C. under nitrogen to a stirred suspension of potassium hydride (1.53 g) in tetrahydrofuran (100 ml). After the addition the mixture was stirred for 15 minutes and then cooled to −78° C. Tert-butyl lithium (17.0 ml of a 1.5M solution in pentane) was added dropwise and after stirring for 45 minutes at this temperature dimethylformamide (4.7 ml) was added. The temperature was maintained at −78° C. for 1 hour and then the reaction mixture was allowed to warm slowly to ambient temperature. The mixture was quenched by the careful addition of 1M hydrochloric acid (200 ml). The organic layer was separated, washed with water, saturated bicarbonate, brine and then dried, filtered and evaporated to give a waxy red solid which was purified by flash column chromatography on silica using 20% ethyl acetate in petroleum ether, b.p. 260–280° C. as the mobile phase to give 3-(4-formylphenyl-1H-[1]benzothieno[3,2-c]pyrazole, m.p. 261–263° C.

d) A solution of the product from c) (100 mg), 3-(1-imidazolyl)propylamine (58 mg) in 1,2-dichloroethane containing glacial acetic acid (0.03 ml) was stirred at ambient temperature for 1 hour. Sodium triacetoxyborohydride (84 mg) was added and the mixture was stirred at ambient temperature for 16 hours. Additional sodium triacetoxyborohydride (90 mg) was added and the mixture was stirred at ambient temperature for 24 hours. The mixture was poured into a stirred solution of saturated aqueous sodium bicarbonate (approx. 20 ml). The organic layer was separated and the aqueous layer was extracted with dichloromethane. The combined organic layer and extracts were washed with water, dried and evaporated under reduced pressure to give a solid which was dissolved in ethanol (15 ml) and 2 drops of concentrated hydrochloric acid were added. The solution was concentrated under reduced pressure to give a solid which was triturated with diethylether, filtered and dried to give 4-(1H-[1]benzothieno[3,2-c]pyrazol-3-yl)-N-[3-(imidazol-1-yl)propyl]benzylamine trihydrochloride, m.p. 206–208° C. (with decomposition).

EXAMPLE 15

This example was prepared in a similar manner to Example 14 by reacting 3-(4-formylphenyl)-1H-[1]benzothieno[3,2-c]pyrazole with 2-morpholinoethylamine to give 4-(1H-[1]benzothieno[3,2-c]pyrazol-3-yl)-N-(2-morpholinoethyl)benzylamine trihydrochloride, m.p. 270–272° C.

Other compounds which were prepared by the methods described above are listed in Table III.

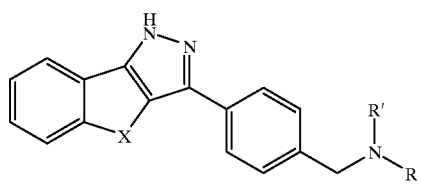

TABLE III

| Example | X | NRR' |
|---|---|---|
| 16 | CH$_2$ | HN–CH$_2$CH$_2$–(4-pyridyl) |
| 17 | S | HN–(5-pyridyl-2-NEt$_2$) |
| 18 | S | HN–CH$_2$CH$_2$–(4-pyridyl) |
| 19 | CMe$_2$ | HN–CH$_2$CH$_2$–NMe$_2$ |
| 20 | CMe$_2$ | HN–(4-pyridyl) |
| 21 | SO$_2$ | HN–(4-pyridyl) |
| 22 | S | HN–(4-pyridyl) |
| 23 | CH$_2$ | HN–(4-pyridyl) |
| 24 | C=O | HN–(4-pyridyl) |
| 25 | O | HN–(4-pyridyl) |
| 26 | S=O | HN–(4-pyridyl) |
| 27 | S | HN–(2-pyridyl) |
| 28 | S | HN–(3-pyridyl) |
| 29 | S | HN–CH$_2$–(4-pyridyl) |
| 30 | S | HN–CH$_2$CH$_2$–NMe$_2$ |
| 31 | CH$_2$ | HN–(3-pyridyl-2-NEt$_2$) |
| 32 | CH$_2$ | HN–(5-pyridyl-2-NEt$_2$) |
| 33 | CH$_2$ | HN–(3-pyridyl-2-OMe) |
| 34 | S | HN–(5-pyridyl-2-Cl) |

TABLE III-continued

| Example | X | NRR' |
|---|---|---|
| 35 | S | 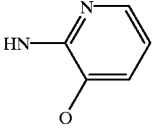 |
| 36 | S | 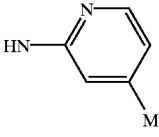 |
| 37 | S | 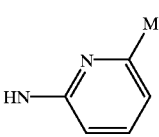 |
| 38 | S | 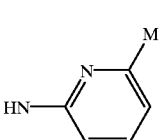 |
| 39 | S | 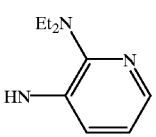 |
| 40 | S | 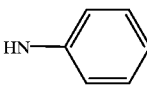 |
| 41 | $CH_2$ | 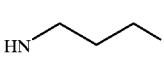 |
| 42 | $CH_2$ | 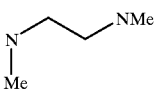 |
| 43 | $CH_2$ | 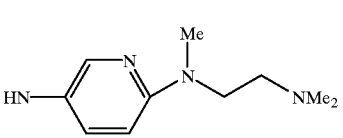 |
| 44 | S | 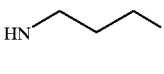 |
| 45 | S | 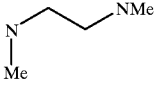 |
| 46 | S | 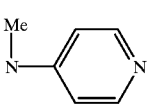 |
| 47 | S | 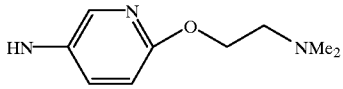 |
| 48 | S | 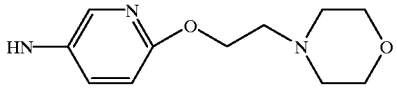 |
| 49 | S | 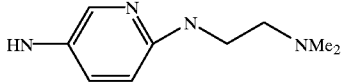 |
| 50 | S | 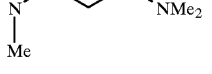 |
| 51 | S |  |
| 52 | S |  |
| 53 | $CH_2$ | 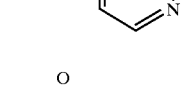 |
| 54 | $CH_2$ | 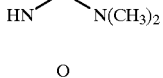 |
| 55 | $CH_2$ | 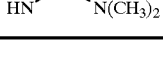 |

Example A

The use of compounds of the present invention in the manufacture of pharmaceutical composition is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

b) Tablets

Tablets are prepared from the following ingredients.

|  | Parts by weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognise or be able to ascertain using no more than routine experimentation, many equivalents to the specific embodiments of the invention described specifically herein. Such equivalents are intended to be encompassed in the scope of the claims.

What is claimed is:

1. Compounds formula I

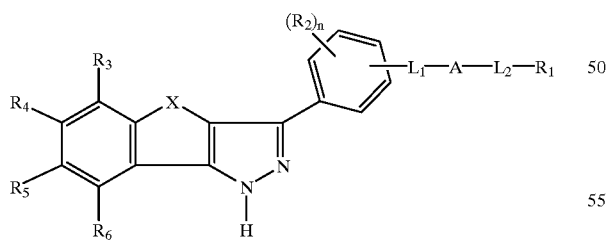

or racemic-diastereomeric mixtures, optical isomers, pharmaceutically-acceptable salts, prodrugs or biologically active metabolites thereof in which $L_1$ represents a group of formula $(E)_s(CH_2)_q$ in which E represents $NR_{24}$, O or S, s is 0 or 1 and q is an integer from 0 to 6, provided that when s is 1 q is at least 1, in which the alkylene chain is optionally substituted by one or more of the following: a $C_{1-6}$ alkyl group optionally substituted by one or more hydroxy, halo or optionally substituted amino; a $C_{1-6}$ alkoxy group optionally substituted by one or more hydroxy, halo or optionally substituted amino; hydroxy; halo; or optionally substituted amino;

A represents CONH, NHCO, $SO_2NH$, $NHSO_2$, or $NR_{25}$;

$L_2$ represents C(=O), C(=NH), or a group of formula $(CH_2)_r$ in which r is an integer from 0 to 6 in which the alkylene chain is optionally substituted by one or more of the following: a $C_{1-6}$ alkyl group optionally substituted by one or more hydroxy, halo or optionally substituted amino; a $C_{1-6}$ alkoxy group optionally substituted by one or more hydroxy, halo or optionally substituted amino; hydroxy; halo; or optionally substituted amino;

$R_2$ represents a $C_{1-6}$ alkyl group optionally substituted by one or more of the following: halo, hydroxy, $C_{1-6}$ alkoxy or optionally substituted amino; a $C_{1-6}$ alkoxy group optionally substituted by one or more of the following: halo, hydroxy, $C_{1-6}$ alkoxy or optionally substituted amino; or $R_2$ is halo, hydroxy, cyano, nitro, carbamoyl, a $C_{1-6}$ alkanoylgroup, a ($C_{1-6}$ alkoxy) carbonyl group or optionally substituted amino;

n represents 0,1,2 or 3

X represents a) substituted methylene b) carbonyl, c) oxygen, d) a group of formula —C=NOR$_7$ in which $R_7$ represents H or a $C_{1-6}$ alkyl group, e) a group of formula $NR_8$ in which $R_8$ represents H, an optionally substituted $C_{1-6}$ alkyl group or optionally substituted phenyl, f) a group of formula $(CH_2)_n$ in which n is 1, 2 or 3, or g) a group of formula $S(O)_p$ in which p is 0, 1 or 2;

$R_3$, $R_4$, $R_5$ and $R_6$ independently represent a) H, b) halo, c) $C_{1-6}$ alkyl group optionally substituted by one or more of the following: hydroxy, a $C_{1-6}$ alkoxy group, halo or an optionally substituted amino group d) a $C_{1-6}$ alkoxy group optionally substituted by one or more of the following: hydroxy; a $C_{1-6}$ alkoxy group; halo; or an optionally substituted amino group provided that these groups are not attached to the carbon which is attached to the oxygen of the alkoxy group; e) optionally substituted phenoxy, f) hydroxy, g) a group formula $COR_a$ in which $R_a$ represents hydroxy, a $C_{1-6}$ alkoxy group or $R_a$ represents an optionally substituted amino group, h) an optionally substituted amino group i) a $C_{1-6}$ alkanoyl group j) nitro, k) optionally substituted phenyl $C_{1-6}$ alkyl, l) optionally substituted phenyl $C_{1-6}$ alkoxy m) cyano; or o) a $C_{2-4}$ alkenyl group or a $C_{2-4}$ alkynyl group each of which is optionally substituted by phenyl which is optionally substituted by one or more of the following: a $C_{1-6}$ alkyl group, a $C_{1-6}$ alkoxy group or halo; and 1) when A is $SO_2NH$, or $NHSO_2$:

$R_1$ represents a) optionally substituted phenyl b) optionally substituted heteroaryl, c) a five, six, seven or eight membered saturated heterocyclic ring containing a nitrogen atom which optionally contains an additional hetero atom selected from O, S or N and is optionally substituted by a $C_{1-6}$ alkyl group wherein said saturated ring may be attached through carbon or a hetero atom d) an optionally substituted amino group or e) a $C_{1-6}$ alkoxy group;

2) when A represents CONH or NHCO:

$R_1$ represents a) phenyl substituted by nitro or one or more $C_{1-6}$ alkoxy groups optionally substituted by one or more of the following: halo, hydroxy, $C_{1-6}$ alkoxy or optionally substituted amino b) optionally substituted heteroaryl or c) a five, six, seven or eight membered saturated heterocyclic ring containing a nitrogen atom which optionally contains an additional hetero atom selected from O, S or N and is optionally substituted by a $C_{1-6}$ alkyl group wherein said saturated ring is attached through a carbon atom or d) a $C_{1-6}$ alkoxy group;

3) when A represents a group $NR_{25}$ and q is at least 1:
$R_1$ represents a) optionally substituted phenyl b) optionally substituted heteroaryl or c) optionally substituted amino group; and 4) when A represents a group $NR_{25}$ and q is 0 and s is 0 then $R_1$ represents optionally substituted heteroaryl;

$R_{24}$ and $R_{25}$ independently represent H; a $C_{1-6}$ alkyl group optionally substituted by one or more of the following: hydroxy, a $C_{1-6}$ alkoxy group, halo or an optionally substituted amino group; a $C_{1-6}$ alkanoyl group or a $C_{1-6}$ alkylsulphonyl group; provided that no two hereto atoms are attached to the same sp3 hybridized carbon atom.

2. Compounds according to claim 1 in which X is $CH_2$ or S.

3. Compounds according to claim 1 in which X is $CH_2$ and A is $NR_{25}$.

4. Compounds according to claim 1 in which X is S and A is $NR_{25}$.

5. Compounds according to claim 1 in which X is $CH_2$ and A is $HNSO_2$.

6. Compounds according to claim 1 in which X is $CH_2$ and A is $SO_2NH$.

7. Compounds according to claim 1 in which X is $CH_2$ and A is CONH.

8. Compounds according to claim 1 in which X is $CH_2$ and A is HNCO.

9. Compounds according to claim 1 in which X is $CH_2$, A is $NR_{25}$, $L_1$ is $(CH_2)_q$ in which q is an integer from 1 to 6 and the alkylene chain is optionally substituted by one or more of the following: a $C_{1-6}$ alkyl group optionally substituted by one or more hydroxy, halo or optionally substituted amino; a $C_{1-6}$ alkoxy group optionally substituted by one or more hydroxy, halo or optionally substituted amino; hydroxy; halo; or optionally substituted amino; $L_2$ is a bond and $R_1$ is optionally substituted pyridyl.

10. A compound selected from:
4-(1,4-dihydroindeno[1,2-c]pyrazole)-N-(4-pyridyl) benzylamine
N-[4-(1,4-dihydroindeno[1,2-c]pyrazol-3-yl)phenyl] benzenesulphonamide
4-(1,4-dihydroindeno[1,2-c]pyrazol-3-yl)-N-(2-methoxyethyl)benzamide
4-(1,4-dihydroindeno[1,2-c]pyrazol-3-yl)-N-(4-nitrophenyl)benzamide
4-(1,4-dihydroindeno[1,2-c]pyrazol-3-yl)imidazol-1-ylacetanilide
4-(1,4-dihydroindeno[1,2-c]pyrazol-3-yl)-N-[2-(imidazol-1-yl)ethyl]aniline
4-(1,4-dihydroindeno[1,2-c]pyrazol-3-yl)-N-(2-morpholinoethyl)benzenesulphonamide
4-(1,4-dihydroindeno[1,2-c]pyrazol-3-yl)-N-(2-methoxyethyl)benzenesulphonamide
N-[2-(N,N-diethylamino)ethyl]-4-(1,4-dihydroindeno[1,2-c]pyrazol-3-yl)benzylamine
N-[2-(N,N-diethylamino)ethyl]-4-(1,4-dihydroindeno[1,2-c]pyrazol-3-yl)benzenesulphonamide
4-(1,4-dihydroindeno[1,2-c]pyrazol-3-yl)-N-(2-morpholinoethyl)benzylamine
N-(4-ethoxyphenyl)-4-(1,4-dihydroindeno[1,2-c]pyrazol-3-yl)benzylamine
(S)-4-(1,4-dihydroindeno[1,2-c]pyrazol-3-yl)-N-(pyrrolidin-2-ylmethyl)benzamide
4-(1H-[1]benzothieno[3,2-c]pyrazol-3-yl)-N-[3-(imidazol-1-yl)propyl]benzylamine
4-(1H-[1]benzothieno[3,2-c]pyrazol-3-yl)-N-(2-morpholinoethyl)benzylamine, and racemic-diastereomeric mixtures, optical isomers, pharmaceutically-acceptable salts, prodrugs and biologically active metabolites thereof.

11. A compound of claim 1 represented by the following structural formula:

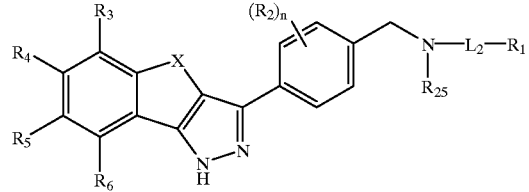

or racemic-diastereomeric mixtures, optical isomers, pharmaceutically-acceptable salts, prodrugs or biologically active metabolites thereof, wherein:

$R_2$ for each occurrence, independently represents a halo; hydroxy; cyano; nitro; carbamoyl; a $C_{1-6}$ alkanoyl-group; a ($C_{1-6}$ alkoxy)carbonyl group; an optionally substituted amino; or a $C_{1-6}$ alkyl group optionally substituted by one or more of the following: halo, hydroxy, $C_{1-6}$ alkoxy or optionally substituted amino; a $C_{1-6}$ alkoxy group optionally substituted by one or more of the following: halo, hydroxy, $C_{1-6}$ alkoxy or optionally substituted amino; and n represents 0,1,2 or 3;

X represents a) methylene which is optionally substituted with a $C_{1-6}$ alkyl group, b) carbonyl, c) oxygen, d) a group of formula —C=$NOR_7$ in which $R_7$ represents H or a $C_{1-6}$ alkyl group, e) a group of formula $NR_8$ in which $R_8$ represents H, an optionally substituted $C_{1-6}$ alkyl group or optionally substituted phenyl, or f) a group of formula $S(O)_p$ in which p is 0, 1 or 2;

$R_3$, $R_4$, $R_5$ and $R_6$ independently represent a) H, b) halo, c) a $C_{1-6}$ alkyl group optionally substituted by one or more of the following: hydroxy, a $C_{1-6}$ alkoxy group, halo or an optionally substituted amino group d) a $C_{1-6}$ alkoxy group optionally substituted by one or more of the following: hydroxy; a $C_{1-6}$ alkoxy group; halo; or an optionally substituted amino group provided that these groups are not attached to the carbon which is attached to the oxygen of the alkoxy group; e) optionally substituted phenoxy, f) hydroxy, g) a group formula $COR_a$ in which $R_a$ represents hydroxy, a $C_{1-6}$ alkoxy group or $R_a$ represents an optionally substituted amino group, h) an optionally substituted amino group i) a $C_{1-6}$ alkanoyl group j) nitro, k) optionally substituted phenyl $C_{1-6}$ alkyl, l) optionally substituted phenyl $C_{1-6}$ alkoxy m) cyano; or o) a $C_{2-4}$ alkenyl group or a $C_{2-4}$ alkynyl group each of which is optionally substituted by phenyl which is optionally substituted by one or more of the following: a $C_{1-6}$ alkyl group, a $C_{1-6}$ alkoxy group or halo;

$L_2$ is a single bond, C(=O), C(=NH), or a $C_{1-6}$ alkyl group;

$R_{25}$ is H, a $C_{1-6}$ alkyl or $C_{1-6}$ alkanoyl; and $R_1$ is an optionally substituted phenyl, an optionally substituted heteroaryl, or an optionally substituted amino group.

12. The compound of claim 11, wherein:

X is S or $CH_2$; and $R_{25}$ is H.

13. The compound of claim 12, wherein:

$R_1$ is an optionally substituted pyridyl; and $L_2$ is a single bond or $CH_2$.

14. The compound of claim 12, wherein:

$R_1$ is an optionally substituted phenyl; and $L_2$ is a single bond or a $CH_2$.

15. The compound of claim 12, wherein:

$R_1$ is an amine represented by the formula $NR_{28}R_{29}$, wherein $R_{28}$ and $R_{29}$ are each, independently H or a $C_{1-6}$ alkyl; and $L_2$ is a $C_{2-5}$ alkyl group.

16. The compound of claim 11, wherein the compound is represented by the following structural formula:

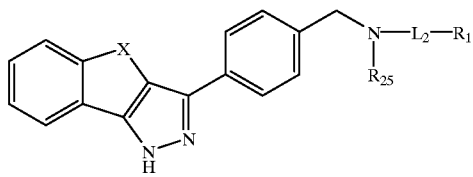

or racemic-diastereomeric mixtures, optical isomers, pharmaceutically-acceptable salts, prodrugs or biologically active metabolites thereof, wherein:

X represents a) a methylene which is optionally substituted with a $C_{1-6}$ alkyl, b) carbonyl, c) oxygen, or d) a group of formula $S(O)_p$.

17. The compound of claim 16, wherein the compound is represented by the following structural formula:

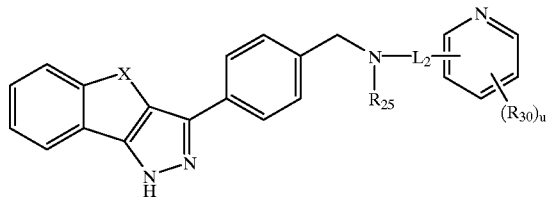

or racemic-diastereomeric mixtures, optical isomers, pharmaceutically-acceptable salts, prodrugs or biologically active metabolites thereof, wherein:

$R_{30}$ for each occurrence, independently, represents a) an amine which is optionally mono- or disubstituted with an independently selected $C_{1-6}$ alkyl, b) a $C_{1-6}$ alkoxy which is optionally substituted with a five, six, seven or eight membered heterocyclic group containing one or more hetero atoms independently selected from and N, O, and S, or an amine represented by the formula $NR_{28}R_{29}$, c) a halo, d) hydroxy, or e) a $C_{1-6}$ alkyl which is optionally substituted with a five, six, seven or eight membered heterocyclic group containing one or more hetero atoms independently selected from N, O and S or an amine represented by the formula $NR_{28}R_{29}$;

$R_{28}$ and $R_{29}$ for each occurrence are, independently, H or a $C_{1-6}$ alkyl; and u is 0, 1, 2, 3, or 4.

18. The compound of claim 17, wherein X is S or $CH_2$.

19. The compound of claim 16, wherein the compound is represented by the following structural formula:

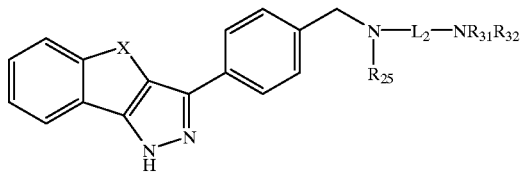

or racemic-diastereomeric mixtures, optical isomers, pharmaceutically-acceptable salts, prodrugs or biologically active metabolites thereof, wherein:

$R_{31}$ and $R_{32}$ are each, independently H or a $C_{1-6}$ alkyl which is optionally substituted with a) an amine represented by the formula $NR_{28}R_{29}$, b) a $C_{1-6}$ alkoxy which is optionally substituted with a five, six, seven or eight membered heterocyclic group containing one or more hereto atoms independently selected from N, O, and S or an amine represented by the formula $NR_{28}R_{29}$, c) a halo, d) hydroxy, e) a $C_{1-6}$ alkyl; or f) a five, six, seven, or eight membered heterocyclic group containing one or more hereto atoms independently selected from N, O and S; and $R_{28}$ and $R_{29}$ for each occurrence are, independently, H or a $C_{1-6}$ alkyl.

20. The compound of claim 19, wherein X is S or $CH_2$.

21. A compound of the following formula wherein X, R and R' are selected form:

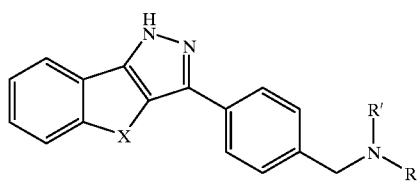

| X | NRR' |
|---|---|
| $CH_2$ | 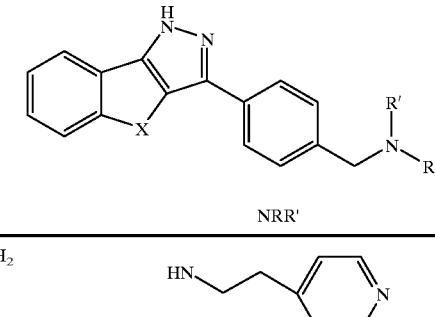 |
| S | |
| S | |
| $CMe_2$ | 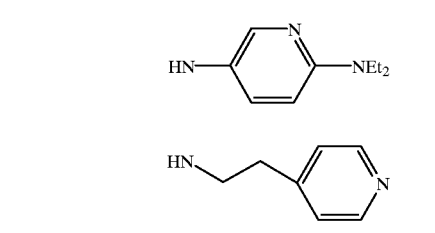 |

-continued

| X | NRR' |
|---|---|
| CMe₂ | HN—(4-pyridyl) |
| SO₂ | HN—(4-pyridyl) |
| S | HN—(4-pyridyl) |
| CH₂ | HN—(4-pyridyl) |
| C=O | HN—(4-pyridyl) |
| O | HN—(4-pyridyl) |
| S=O | HN—(4-pyridyl) |
| S | HN—(2-pyridyl) |
| S | HN—(3-pyridyl) |
| S | HN—CH₂—(4-pyridyl) |
| S | HN—CH₂CH₂—NMe₂ |
| CH₂ | HN—(2-(NEt₂)-pyridin-3-yl) |

-continued

| X | NRR' |
|---|---|
| CH₂ | HN—(6-NEt₂-pyridin-3-yl) |
| CH₂ | HN—(2-MeO-pyridin-3-yl) |
| S | HN—(6-Cl-pyridin-3-yl) |
| S | HN—(3-OH-pyridin-2-yl) |
| S | HN—(4-Me-pyridin-2-yl) |
| S | HN—(6-Me-pyridin-2-yl) |
| S | HN—(4,6-diMe-pyridin-2-yl) |
| S | HN—(2-NEt₂-pyridin-3-yl) |
| S | HN—(4-MeO-phenyl) |
| CH₂ | HN—CH₂CH₂CH₂—NMe₂ |

-continued

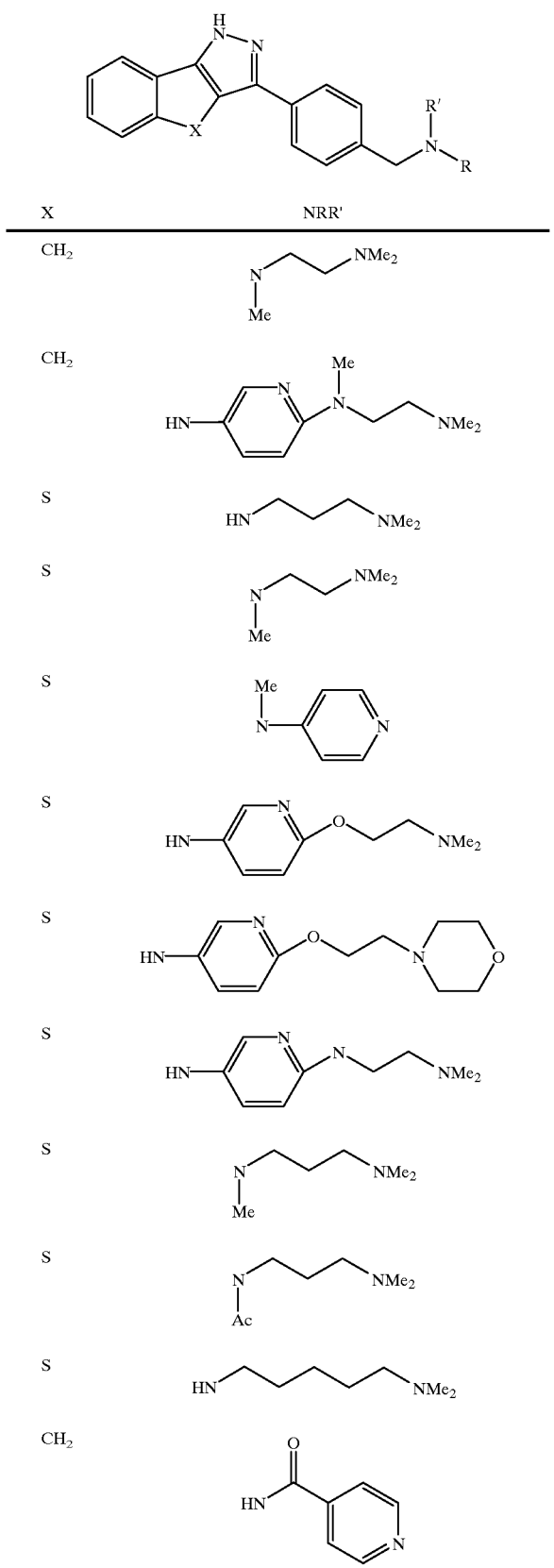

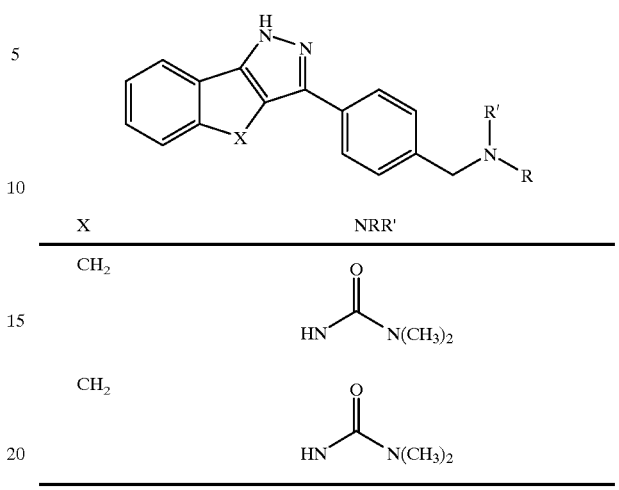

and racemic-diastereomeric mixtures, optical isomers, pharmaceutically-acceptable salts, prodrugs and biologically active metabolites thereof.

22. A pharmaceutical composition comprising a pharmaceutically acceptable diluent or carrier and a compound of claim 1.

23. A method of inhibiting one or more protein kinase activity in a patient comprising the step of administering to said patient a therapeutically effective amount of a compound of claim 1 or racemic-diastereomeric mixtures, optical isomers, pharmaceutically-acceptable salts, prodrugs or biologically active metabolites thereof to said patient.

24. The method of claim 23 wherein said tyrosine kinase is selected from the group consisting of KDR, FGFR-1, PDGFRβ, PDGFRα, IGF-1R, c-Met, flt-1, Flt-4 TIE-2, TIE-1 Lck, Src, fyn, Lyn, Blk, Hck, fgr and yes.

25. A method of affecting angiogenesis in a patient comprising the step of administering to said patient a therapeutically effective amount of a compound of claim 1 or racemic-diastereomeric mixtures, optical isomers, pharmaceutically-acceptable salts, prodrugs or biologically active metabolites thereof to said patient.

26. The method of claim 23 wherein said protein kinase is a serine/threonine kinase or a protein tyrosine kinase.

27. A method of inhibiting the progression of a disease state in a patient comprising the step of administering to said patient a therapeutically effective amount of a compound of claim 1 or racemic-diastereomeric mixtures, optical isomers, pharmaceutically-acceptably salts, prodrugs or biologically active metabolites thereof to said patient, wherein said disease state is selected from the group consisting of cancer, rheumatoid arthritis, atherosclerosis, psoriasis, hemangioma, myocardial angiogenesis, coronary and cerebral collateral vascularization, ischemia, corneal disease, rubeosis, neovascular glaucoma, macular degeneration, retinopathy of prematurity, wound healing, ulcer Helicobacter related diseases, fractures, endometriosis, a diabetic condition, cat scratch fever, thyroid hyperplasia, asthma or endema following burns, trauma, chronic lung disease, stroke, polyps, cysts, synovitis, chronic and allergic inflammation, ovarian hyperstimulation syndrome, pulmonary and cerebral edema, keloid, fibrosis, cirrhosis, carpal tunnel syndrome, adult respiratory distress syndrome, ascites, an ocular condition, a cardiovascular condition, Crow-Fukase (POEMS) syndrome, sickle cell anaemia, systemic lupus, glomerulonephritis, synovitis, inflammatory bowel disease, Crohn's disease, glomerulonephritis, osteoarthritis, multiple sclerosis, graft rejection, Lyme disease, sepsis, von Hippel Lindau disease, pemphigoid, Paget's disease, polycystic kidney disease, sarcoidosis, thyroiditis, hyperviscosity syndrom, Osler-Weber-Rendu disease, chronic occlusive pulmonary disease, radiation, hypoxia, preeclampsia, menometrorrhagia, endometriosis, infection by Herpes simplex, Herpes Zoster, human immunodeficiency virus, parapoxvirus, protozoa, toxoplasmosis, and tumor-associated effusions and edema.

28. The method of claim 27 wherein the ocular condition is ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy or macular degeneration.

29. The method of claim 27 wherein the cardiovascular condition is atherosclerosis, restenosis, ischemia/reperfusion injury, vascular occlusion or carotid obstructive disease.

30. The method of claim 27 wherein the cancer is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, Kaposi's sarcoma, Hodgkin's disease, lymphoma, myeloma, leukemia or malignant ascites.

31. The method of claim 27 wherein the diabetic condition is insulin-dependent diabetes mellitus glaucoma, diabetic retinopathy or microangiopathy.

32. A method of decreasing fertility in a patient, said method comprising the step of administering to the patient an effective amount of a compound of claim 1 or racemic-diastereomeric mixtures, optical isomers, pharmaceutically-acceptable salts, prodrugs or biologically active metabolites thereof.

33. The method of claim 25 wherein the compound or a physiologically acceptable salt, prodrug or biologically active metabolite thereof is administered in an amount effective to promote angiogenesis or vasculogenesis.

34. The method of claim 26 wherein the protein kinase is Tie-2.

35. The method of claim 33 wherein the compound of Formula I, or physiologically acceptable salt, prodrug or biologically active metabolite thereof, is administered in combination with a pro-angiogenic growth factor.

36. The method of claim 35 wherein the pro-angiogenic growth factor is selected from the group consisting of VEGF, VEGF-B, VEGF-C, VEGF-D, VEGF-E, HGF, FGF-1, FGF-2, derivatives thereof and antiiodotypic antibodies.

37. The method of claim 33 wherein the patient is suffering from anemia, ischemia, infarct, transplant rejection, a wound, gangrene or necrosis.

38. The method of claim 23 wherein the protein kinase activity is involved in T cell activation, B cell activation, mast cell degranulation, monocyte activation, the potentiation of an inflammatory response or a combination thereof.

39. A method of inhibiting vascular hyperpermeability or the production of edema in a patient comprising the step of administering to said patient a therapeutically effective amount of a compound of claim 1 or racemic-diastereomeric mixtures, optical isomers, pharmaceutically-acceptable salts, prodrugs or biologically active metabolites thereof to said patient.

40. A method of affecting hyperproliferative disorders in patient comprising the step of administering to said patient a therapeutically effective amount of a compound of claim 1 or racemic-diastereomeric mixtures, optical isomers, pharmaceutically-acceptable salts, prodrugs or biologically active metabolites thereof to said patient.

41. A method of treating one or more ulcers in a patient comprising the step of administering to said patient a therapeutically effective amount of a compound of claim 1 or racemic-diastereomeric mixtures, optical isomers, pharmaceutically-acceptable salts, prodrugs or biologically active metabolites thereof to said patient.

42. The method of claim 41, wherein the ulcer or ulcers are caused by a bacterial or fungal infection; or the ulcer or ulcers are Mooren ulcers; or the ulcer or ulcers are a symptom of ulcerative colitis.

* * * * *